United States Patent [19]
Yoshida et al.

[11] Patent Number: 6,044,689
[45] Date of Patent: Apr. 4, 2000

[54] APPARATUS FOR SENSING LOW CONCENTRATION NOX, CHAMBER USED FOR APPARATUS FOR SENSING LOW CONCENTRATION NOX; GAS SENSOR ELEMENT AND METHOD OF MANUFACTURING THE SAME; AND AMMONIA REMOVING APPARATUS AND NOX SENSOR UTILIZING THIS APPARATUS

[75] Inventors: Toshihiro Yoshida; Naoyuki Ogawa, both of Nagoya; Tomonori Takahashi, Chita; Shinji Ohtsubo, Nagoya, all of Japan

[73] Assignee: NGK Insulators, Ltd., Nagoya, Japan

[21] Appl. No.: 09/063,471

[22] Filed: Apr. 20, 1998

[30] Foreign Application Priority Data

| Apr. 24, 1997 | [JP] | Japan | 9-107215 |
| Apr. 28, 1997 | [JP] | Japan | 9-110863 |
| Apr. 28, 1997 | [JP] | Japan | 9-110864 |
| Sep. 25, 1997 | [JP] | Japan | 9-259978 |
| Nov. 10, 1997 | [JP] | Japan | 9-307090 |

[51] Int. Cl.[7] .................................................. G01N 24/04
[52] U.S. Cl. ........................... 73/31.03; 422/93; 436/110
[58] Field of Search ................................. 73/23.2, 23.21, 73/23.31, 31.06, 31.03; 422/90, 93; 436/110, 114, 117, 118

[56] References Cited

U.S. PATENT DOCUMENTS

| 4,279,618 | 7/1981 | Barden . | |
| 4,358,950 | 11/1982 | Chang . | |
| 4,458,242 | 7/1984 | Kusanagi et al. . | |
| 4,701,739 | 10/1987 | Sasaki . | |
| 4,713,646 | 12/1987 | Sunano et al. . | |
| 4,816,414 | 3/1989 | Koocher et al. | 436/85 |
| 4,958,514 | 9/1990 | Takami et al. . | |
| 5,211,053 | 5/1993 | Nolting et al. . | |
| 5,302,191 | 4/1994 | Koutrakis et al. | 95/285 |
| 5,389,340 | 2/1995 | Satake . | |
| 5,705,129 | 1/1998 | Takahashi et al. . | |
| 5,854,077 | 12/1998 | Wolfson et al. | 436/110 |

FOREIGN PATENT DOCUMENTS

| 0 632 265 A2 | 4/1995 | European Pat. Off. . |
| 0 737 859 A1 | 10/1996 | European Pat. Off. . |
| A-61-155848 | 7/1961 | Japan . |
| WO91/19975 | 12/1991 | WIPO . |

*Primary Examiner*—Michael Brock
*Attorney, Agent, or Firm*—Wall Marjama Bilinski & Burr

[57] ABSTRACT

The disclosed apparatus for sensing low concentration NOx in a measurement gas especially in the atmosphere has at least a sensor element made of an oxide arranged in a flow path of the measurement gas, the resistance of the sensor element varying in response to changes in NOx concentration in the measurement gas. As suitable options of this type of the NOx sensor, there are disclosed a chamber used for an apparatus for sensing low concentration NOx, a gas sensor element and a method of manufacturing the gas sensor element, and an ammonia removing apparatus and an NOx sensor utilizing the ammonia removing apparatus.

7 Claims, 15 Drawing Sheets

FIG_5

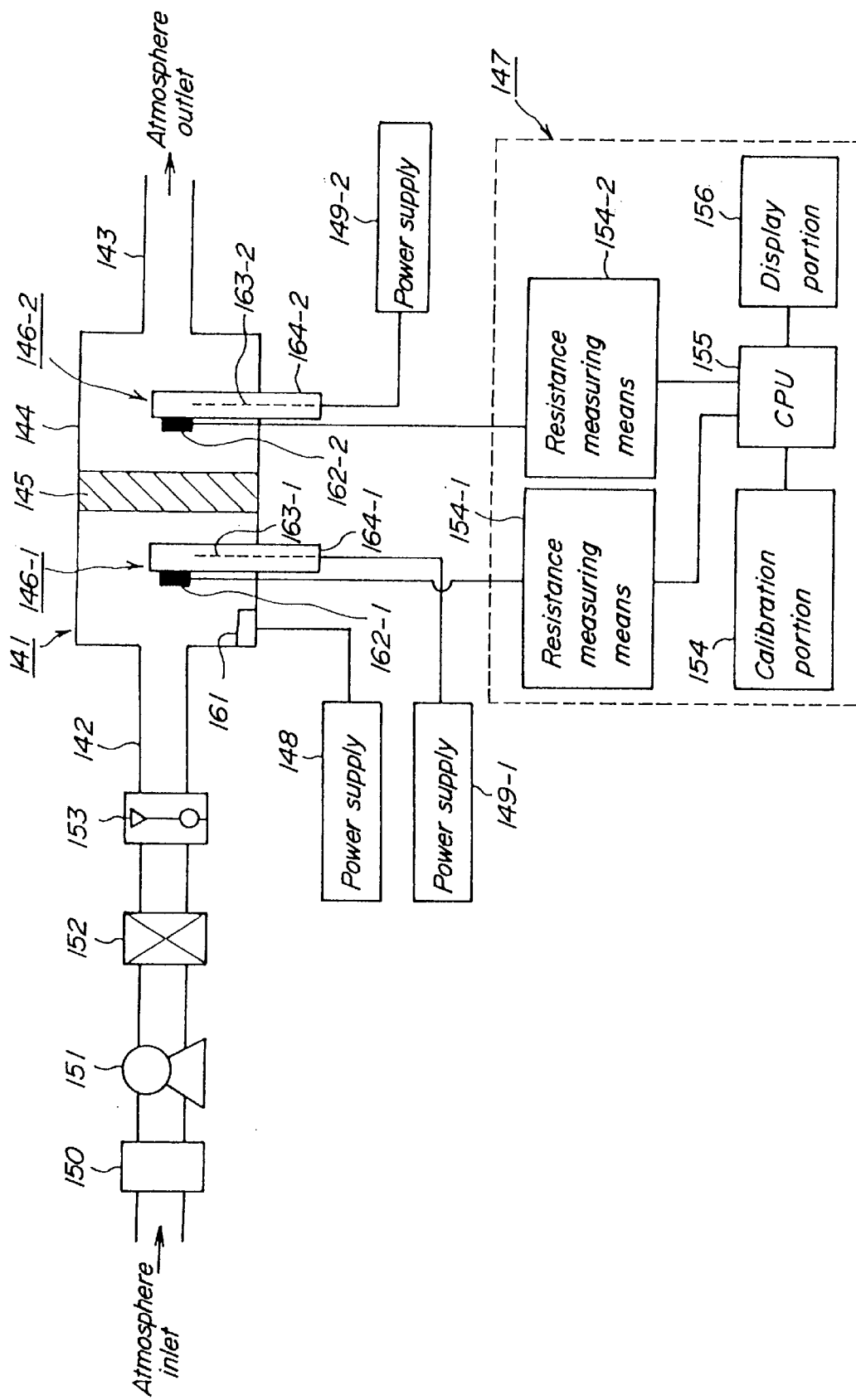

FIG_8a
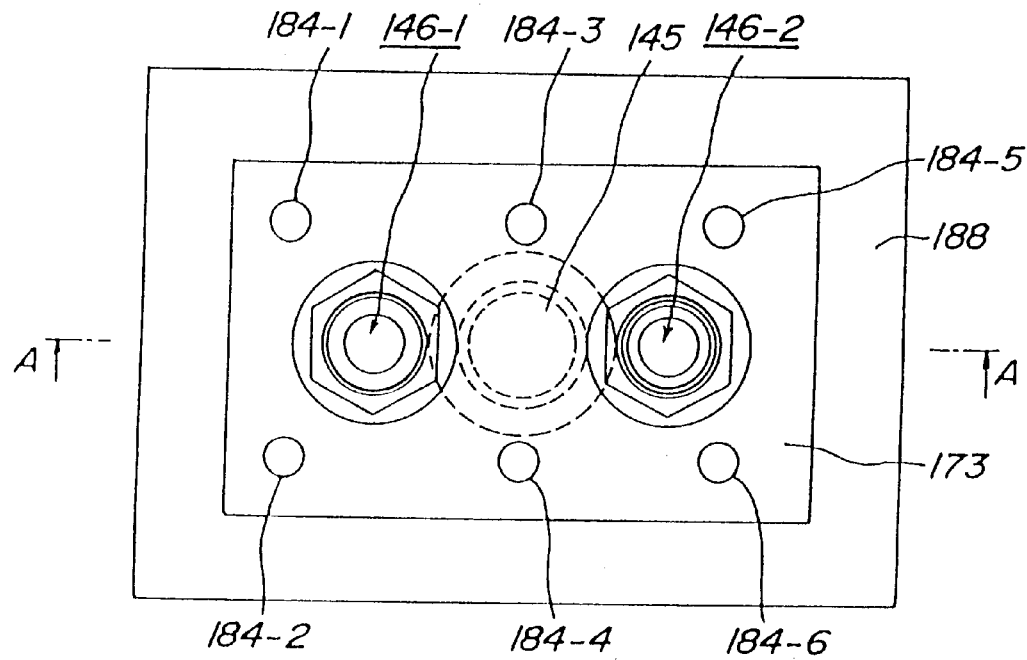
FIG_8b
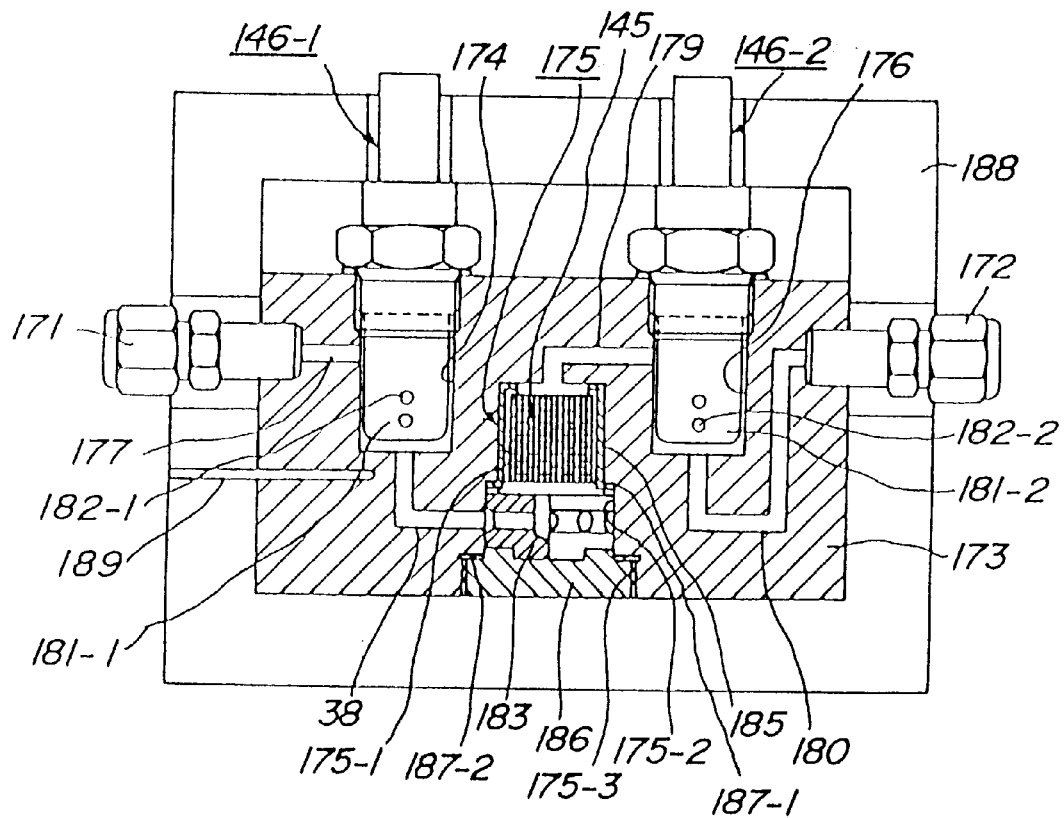

FIG_9a
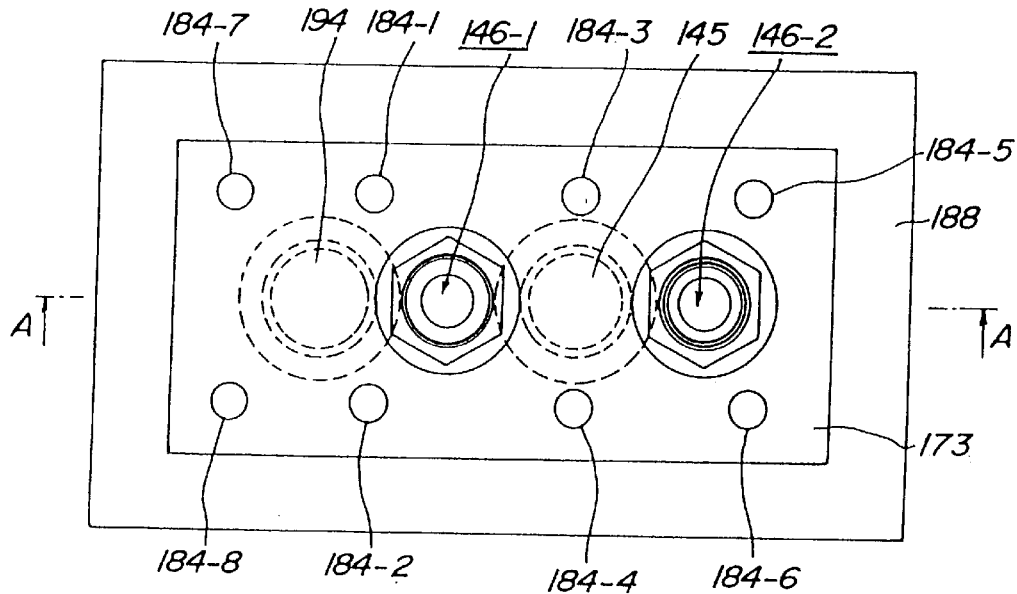
FIG_9b
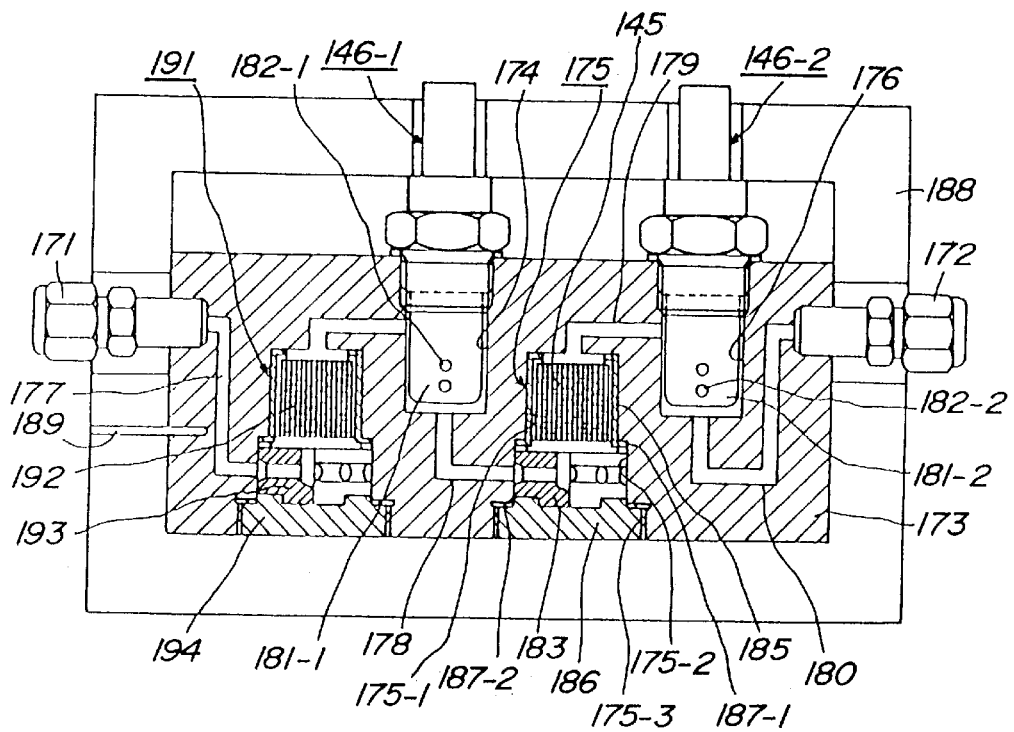

FIG_10
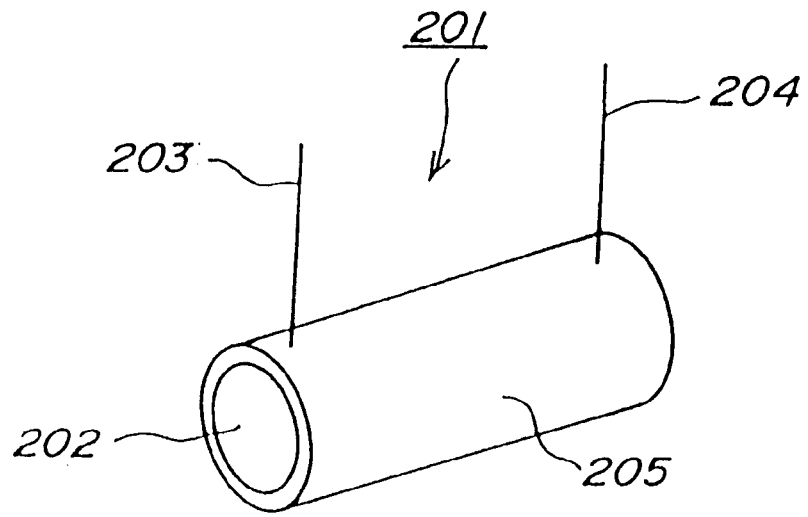
FIG_11
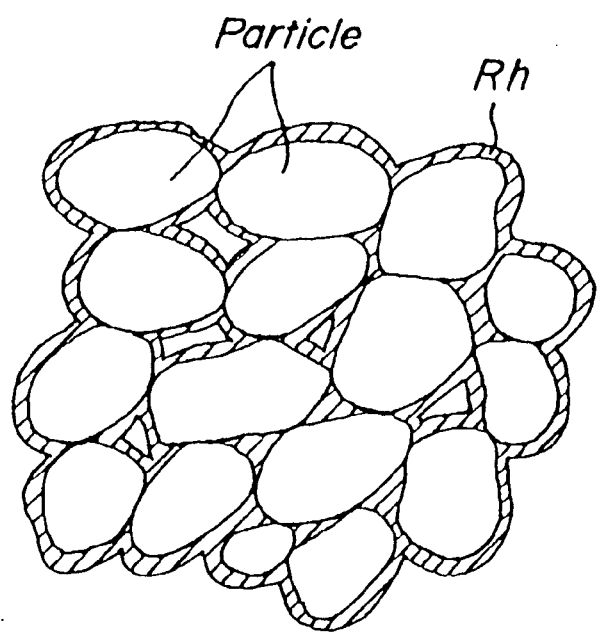

FIG_12
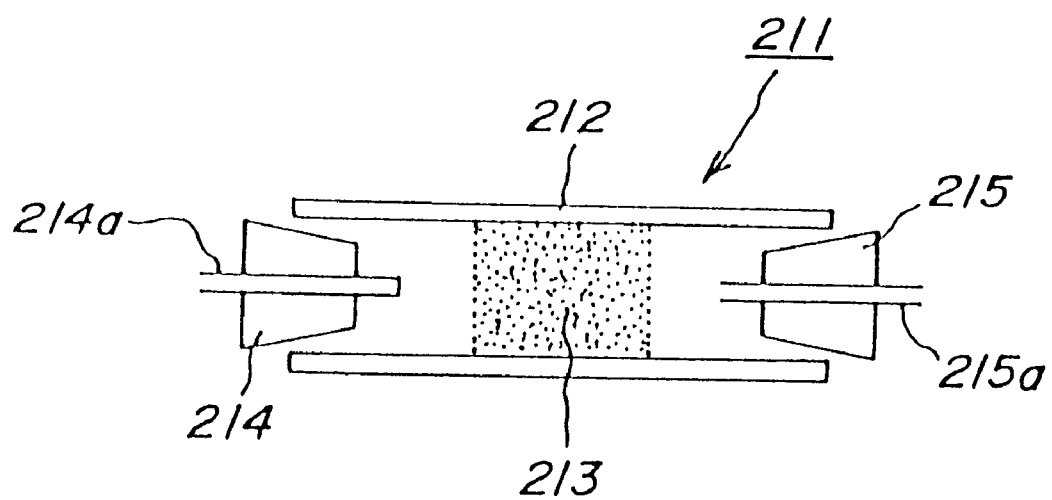

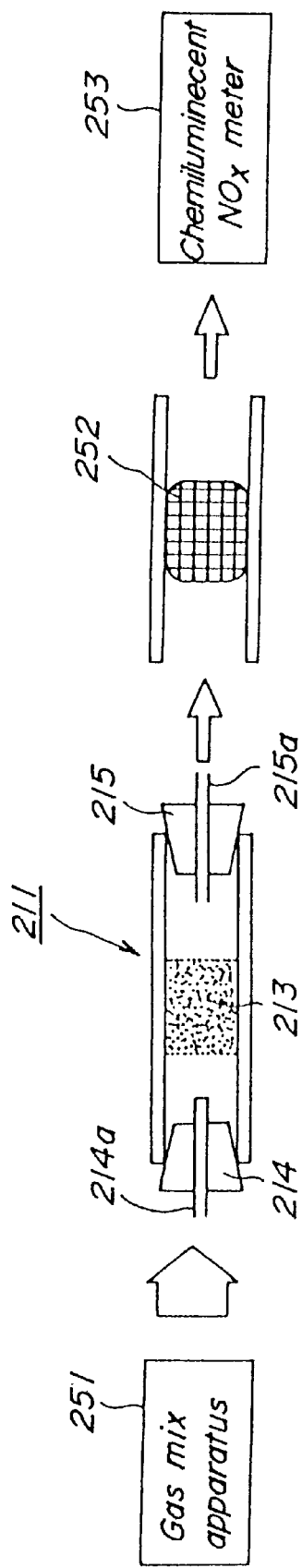
FIG_14

FIG_15
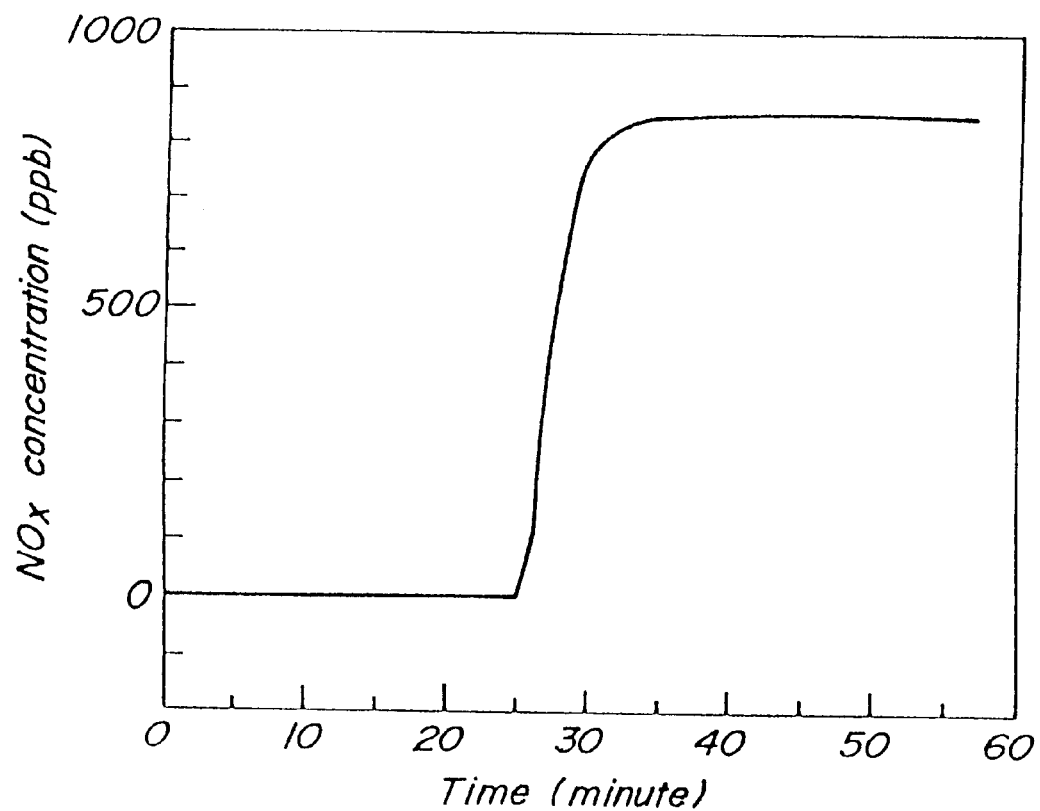

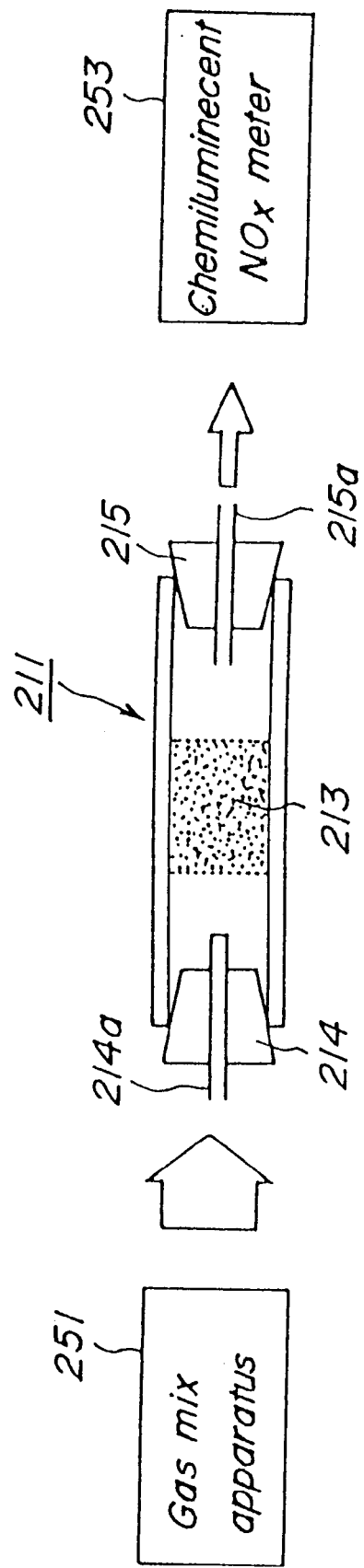

APPARATUS FOR SENSING LOW CONCENTRATION NOX, CHAMBER USED FOR APPARATUS FOR SENSING LOW CONCENTRATION NOX; GAS SENSOR ELEMENT AND METHOD OF MANUFACTURING THE SAME; AND AMMONIA REMOVING APPARATUS AND NOX SENSOR UTILIZING THIS APPARATUS

BACKGROUND OF THE INVENTION

1. Field of the Invention

The present invention relates to an apparatus for sensing NOx in a gas to be measured, having a sensor element made of an oxide, the resistance of the oxide varying in response to changes in NOx concentration of the gas if the oxide is contacted with the gas including NOx, and a measuring portion for measuring a resistance variation of the sensor element and for determining an NOx concentration in the gas to be measured. The present invention especially relates to an apparatus used preferably for sensing low concentration NOx in the atmosphere with respect to the NO concentration and $NO_2$ concentration.

Moreover, the present invention relates to an apparatus for sensing NOx in a gas to be measured, having a sensor element made of an oxide, the resistance of the oxide varying in response to changes in NOx concentration of the gas if the oxide is contacted with the gas including NOx, and especially relates to an apparatus used preferably for sensing low concentration NOx in the atmosphere with respect to the NO concentration and $NO_2$ concentration.

Further, the present invention relates to a chamber used for an apparatus for sensing a low concentration NOx having; a catalyst arranged to maintain partial pressures of NO and $NO_2$ in the atmosphere at an equilibrium state; and sensor elements arranged in a flow path of the atmosphere, the resistance of each of the sensor elements varying in response to changes in NOx concentration of the atmosphere, one sensor element being contacted with the atmosphere which is not contacted with the catalyst and the other sensor element being contacted with the atmosphere which is contacted with the catalyst.

Furthermore, the present invention relates to a gas sensor element made of an oxide and a method of manufacturing the same, the resistance of the oxide varying in response to changes in NOx concentration of the gas to be measured if the oxide is contacted with the gas to be measured.

Moreover, the present invention relates to an ammonia removing apparatus for removing an ammonia component in a gas to be measured such as the atmosphere and an NOx sensor utilizing this ammonia removing apparatus.

2. Description of Related Art

As a method of measuring an NOx concentration in a gas to be measured such as a fired gas from an incinerator, which includes an NOx component such as nitrogen oxide, it is known to sample a gas to be measured, in, a dust chimney, and to measure an NOx concentration of the sampled gas by means of an optical measuring apparatus. However, the optical measuring apparatus is expensive and the response time thereof is long since the sampling operation is necessary.

In order to eliminate the drawbacks mentioned above, it has been proposed to use a direct insertion type semiconductor sensor. For example, in Japanese Patent Laid-Open Publication No. 6-222028 (JP-A-6-222028), an NOx sensor comprising a response portion made of an oxide having a predetermined perovskite structure, and a conductivity measuring portion for measuring a conductivity of the response portion is disclosed.

However, in the direct insertion type semiconductor sensor mentioned above, since a measuring target is an NOx concentration in a combusted exhaust gas flowing through the dust chimney, a temperature of the sensor element is low for example 300–400° C. Therefore, NOx components is not adsorbed to a response portion in an equilibrium state.

This is not a problem if the apparatus is used for sensing an NOx concentration in a combusted exhaust gas having a relatively high NOx concentration. However, this presents a serious problem in an apparatus is used for sensing an NOx concentration in the atmosphere having a low NOx concentration, since it is not possible to measure an NOX concentration in with reliable precision.

Also, in the direct insertion type semiconductor sensor mentioned above, there is no countermeasure for an influence of $O_2$ and CO components included in the gas to be measured with respect to the measured NOx concentration. Moreover, in the response portion, the resistance thereof is varied in response to the concentration of $NOx(NO_2+NO)$. However, if a ratio of partial pressure between $NO_2$ and NO, is varied, the resistance measured by the response portion will vary even for the same NOx amount. In this case, it is reasonable to conclude that the NOx component is not selectively measured. Therefore, in the direct insertion type semiconductor sensor mentioned above, there is a drawback in that the NOx concentration in the gas to be measured cannot be selectively measured in a highly precise manner, despite the fact that the semiconductor sensor is cheap and shows excellent response time as compared with the optical measuring apparatus.

Moreover, in order to solve the drawbacks mentioned above, the applicant discloses, in U.S. Pat. No. 5,705,129, an NOx sensor comprising; an oxide sensor element; a catalyst arranged upstream of the oxide sensor element to maintain partial pressures of NO and $NO_2$ in the measurement gas at an equilibrium state; a heater for controlling a temperature of the oxide sensor element; and an $O_2$ sensor for a correction. However, also in the NOx sensor mentioned above, a target measurement gas is a fired exhaust gas from an incinerator as mentioned above. Therefore, one drawback is that the NOx sensor mentioned above cannot be used for measuring low concentration NOx in the atmosphere which is a target measurement gas of the invention.

Further, the applicant discloses, in Japanese Patent Application No.9-80054, an apparatus for sensing a low concentration NOx having a catalyst arranged to maintain partial pressures of NO and $NO_2$ in the atmosphere at an equilibrium state; and sensor elements arranged in a flow path of the atmosphere, the resistance of each of the sensor elements varying in response to changes in NOx concentration of the atmosphere, a first sensor element being contacted with the atmosphere which is not contacted with the catalyst and a second sensor element being contacted with the atmosphere which is contacted with the catalyst. In the apparatus for sensing a low concentration NOx mentioned above, it is disclosed that the first sensor element, the catalyst and the second sensor element are set in a chamber, but a construction of the chamber is not particularly defined at all. Therefore, it is required to make a construction of the chamber most suitable on making the chamber compact and on improving a measuring precision.

Furthermore, as a gas sensor element, there are known various types of gas sensor elements utilizing an oxide, which resistance is varied in response to changes in concentrations of components in a gas to be measured. As one example of these gas sensor element, there is disclosed in Japanese Patent Laid-Open Publication No. 61 155848 (JP-A-61-155848) a gas sensor utilizing an oxide in which a predetermined element is added in an oxide solid solution of titanium-tin system so as to make possible a measurement in Low temperature and to obtain compact and highly sensitive properties.

The above mentioned gas sensor element utilizing an oxide, in which precious metals are added, can realize the objects mentioned above. However, if it used for measuring an NOx concentration, an interference of SOx, HC and CO with respect to a measurement of NOx concentration becomes larger, and the influence of temperature variation in the case of measuring NOx concentration also becomes larger. Therefore, one drawback is measurement precision becomes worse.

Moreover, heated precious metals and oxides are used for the above mentioned catalyst. In this case, the catalyst functions not only to maintain partial pressures of NO and $NO_2$ in a gas to be measured at an equilibrium state but also to generate an NOx component by oxidizing an ammonia component. As a result, if an ammonia component is existent in a gas to be measured, an NOx concentration in a gas to be measured which is passed through the catalyst becomes a sum of an NOx concentration existent in a gas to be measured from the beginning and an NOx concentration generated by oxidizing an ammonia component. Therefore, it is not possible to measure an NOx concentration of the gas in a highly precise manner.

On the other hand, as a method of removing an ammonia component which is not for an NOx sensor, there are known a method of using an adsorbent and a method of bubbling in an oxidizing solution. However, in the case of using the adsorbent, it is difficult to selectively adsorb an ammonia component and an NOx component is adsorbed together with an ammonia component. Therefore, it is not possible to measure an NOx concentration in a highly precise manner. Moreover, in the case of bubbling in an oxidizing solution, it is difficult to selectively dissolve an ammonia component, and a part of an NOx component is dissolved together with an ammonia component. Therefore, it is also not possible to measure an NOx concentration in a highly precise manner.

SUMMARY OF THE INVENTION

A first object of the invention is to eliminate the drawbacks mentioned above and to provide an apparatus for sensing a low concentration NOx which can measure a low NOx concentration in the atmosphere in a highly precise manner.

A second object of the invention is to eliminate the drawbacks mentioned above and to provide an apparatus for sensing a low concentration NOx which can measure a low NOx concentration in a gas to be measured preferably in the atmosphere in a highly precise manner.

A third object of the invention is to eliminate the drawbacks mentioned above and to provide a chamber used for an apparatus for sensing a low concentration NOx which can realize a compact shape and improve a measurement precision.

A fourth object of the invention is to eliminate the drawbacks mentioned above and to provide a gas sensor element and a method of manufacturing the same, which can improve a measurement precision of an NOx concentration by reducing an interference of SOx, HC, CO gases in the case of measuring an NOx concentration or by reducing an interference of SOx, HC, CO gases and eliminating a temperature dependency in the case of measuring an NOx concentration.

A fifth object of the invention is to eliminate the drawbacks mentioned above and to provide an ammonia removing apparatus for removing an ammonia component and an NOx sensor utilizing the ammonia removing apparatus which can measure an NOx concentration in a highly precise manner without being influenced by an ammonia component.

According to a first aspect of the invention, an apparatus for sensing low concentration NOx in a measurement gas, comprises: a sensor element made of a metal oxide semiconductor arranged in a flow path of the measurement gas, the resistance of the sensor element varying in response to changes in NOx concentration in the measurement gas, wherein a temperature T of the sensor element is maintained in a range of $500°$ C.$\leq T \leq 800°$ C.

According to a second aspect of the invention, an apparatus for sensing low concentration NOx in the atmosphere, comprises: a sensor element made of an oxide arranged in a flow path of the atmosphere, the resistance of the sensor element varying in response to changes in NOx concentration in the atmosphere; a catalyst arranged upstream of a flow path of the atmosphere to maintain partial pressures of NO and $NO_2$ in the atmosphere at an equilibrium state and to remove a combustible gas; and measuring means for receiving a signal from the sensor element being contacted with the atmosphere which is contacted with the catalyst; wherein a temperature T of the sensor element is maintained in a range of $500°$ C.$\leq 800°$ C.

In the apparatus for sensing low concentration NOx according to the first aspect of the invention, an NOx concentration is measured under a condition such that a temperature T of the sensor element is maintained in a range of $500°$ C.$\leq 800°$ C. In the preferred embodiment, a water control means further controls a water component in the atmosphere at constant, and the thus controlled atmosphere is contacted with the sensor element. Therefore, an NOx component is adsorbed at an equilibrium state with respect to a response portion, ant thus it is possible to measure a low concentration NOx in a highly precise manner. Moreover, in the apparatus for sensing low concentration NOx according to the second aspect of the invention, an NOx concentration is measured under a condition such that a temperature T of the sensor element is maintained in a range of $500°$ C.$\leq T \leq 800°$ C. by using the atmosphere which is contacted with the catalyst for maintaining partial pressures of NO and $NO_2$ in the atmosphere at an equilibrium state. In the preferred embodiment, a water control means further controls a water component in the atmosphere at constant, and the thus controlled atmosphere is contacted with the sensor element. Therefore, it is possible to measure a low concentration NOx in the atmosphere in a highly precise manner.

According to a third aspect of the invention, an apparatus for sensing low concentration NOx in a measurement gas, comprises: a gas introduction module for introducing the measurement gas therein from the outside; a humidity control module for controlling a humidity of the measurement gas introduced by said gas introduction module; an NOx measurement module for measuring an NOx concentration in the measurement gas in which humidity is controlled by said humidity control module, comprising a sensor element made of a metal oxide semiconductor arranged in a flow path of the measurement gas, the resistance of the sensor element varying in response to changes in NOx concentration in the measurement gas; and a process and control module for calculating an NOx concentration on the basis of a resistance value measured by the sensor element of the NOx measurement module and for controlling the humidity control module and the NOx measurement module.

In the apparatus for sensing low concentration NOx according to the third aspect of the invention, the NOx measurement module has preferably the catalyst for maintaining partial pressures of NO and $NO_2$ in the measurement gas at an equilibrium state, wherein use is made of two sensor elements, one sensor element being contacted with the measurement gas which is not contacted with the catalyst and the other sensor element being contacted with the measurement gas which is contacted with the catalyst. In addition, the other gas introduction module, humidity control module, and process and control module are controlled most suitably. Therefore, it is possible to measure a low concentration NOx in the atmosphere in a highly precise manner.

According to the invention, a chamber used for an apparatus for sensing low concentration NOx in a measurement gas having, a catalyst arranged to maintain partial pressures of NO and $NO_2$ in the measurement gas at an equilibrium state, and first and second sensor elements arranged in a flow path of the measurement gas, the resistance of each of the first and second sensor elements varying in response to changes in NOx concentration of the measurement gas, the first sensor element being contacted with the measurement gas which is not contacted with the catalyst and the second sensor element being contacted with the measurement gas which is contacted with the catalyst, comprises: a chamber main body having a gas inlet and a gas outlet of the measurement gas; a first sensor element securing portion for securing the first sensor element, arranged in the chamber main body; a catalyst accommodating portion for accommodating the catalyst, arranged in the chamber main body; a second sensor element securing portion for securing the second sensor element, arranged in the chamber main body; and first, second, third and fourth through holes arranged in the chamber main body in such a manner that the first through hole communicates the gas inlet and the first sensor element securing portion, the second through hole communicates the first sensor element securing portion and the catalyst accommodating portion, the third through hole communicates the catalyst accommodating portion and the second sensor element securing portion, and the fourth through hole communicates the second sensor element securing portion and the gas outlet.

In the chamber used for the apparatus for sensing low concentration NOx in a measurement gas according to the invention, the first sensor element securing portion, the catalyst accommodating portion, and the second sensor element securing portion are arranged in the chamber main body, and the first to fourth through holes communicate therebetween to construct integrally the first sensor element, the catalyst, and the second sensor element in the chamber. Therefore, it is possible to achieve a compact chamber construction in comparison to the first sensor element, the catalyst, and the second sensor element are arranged in a chamber having a large inner space.

Moreover, in the case such that a sectional area of the second through hole is smaller than that of the first sensor element securing portion, it is possible to achieve a long flow path. Therefore, the catalyst is not affected by a high temperature of the first sensor element.

According to the invention, a gas sensor element made of an oxide arranged in a flow path of a measurement gas, the resistance of the gas sensor element varying in response to changes in component concentration in the measurement gas, comprises 1–10 atomic % of Ta being existent in the oxide with respect to a metal atom in the oxide.

In the gas sensor element according to the invention, we find that an influence of SOx gas, HC gas or CO gas during an NOx concentration measurement can be reduced by adding 1–10 atomic % of Ta in the oxide preferably made of $SnO_2$. Moreover, in the preferred embodiment, Rh is existent on a particle surface of the oxide and is not existent on a connection portion between particles in addition to an adding of Ta mentioned above. In this case, we find that it is possible to further eliminate a temperature dependency during the NOx concentration measurement.

Moreover, in the preferred embodiment, a firing temperature of the oxide is controlled at higher than 1200° C., a particle size of the oxide fired body is maintained at larger than 0.2 μm, a porosity of the oxide fired body is maintained at larger then 20%, and a short diameter of the oxide fired body is maintained at smaller than 3 μm. In these cases, it is possible to further improve a precision of the NOx concentration measurement. In this case, a short diameter of the oxide fired body means a thickness of a layer of the oxide fired body in the gas sensor element.

According to the invention, a method of manufacturing the gas sensor element, comprises the steps of: preparing an oxide slurry by mixing oxide with a predetermined amount of Ta compound; applying the oxide slurry on a substrate having an electrical insulation property; firing the substrate on which the oxide slurry is applied to obtain an oxide fired body; immersing the oxide fired body in a solution including Rh; and subjecting the thus immersed oxide fired body to a heat treatment.

In the method of manufacturing the gas sensor element according to the invention, we find that it is possible to achieve the construction such that Rh is existent on a particle surface and is not existent on a connection portion between particles, by preparing an oxide slurry by mixing oxide with a predetermined amount of Ta compound, applying the oxide slurry on a substrate having an electrical insulation property, firing the substrate on which the oxide slurry is applied to obtain an oxide fired body, immersing the oxide fired body in a solution including Rh, and subjecting the thus immersed oxide fired body to a heat treatment.

According to the invention, an ammonia removing apparatus for removing an ammonia component from a measurement gas, comprises: an ammonia removing means made of a solid acid compound.

According to the invention, an NOx sensor for sensing an NOx concentration in a measurement gas, comprises: a sensor element made of an oxide semiconductor; a catalyst arranged upstream of the sensor element to maintain partial pressures of NO and $NO_2$ in the measurement gas at an equilibrium state; and the ammonia removing apparatus having the construction mentioned above arranged upstream of said catalyst.

In the ammonia removing apparatus according to the invention, we find that the solid acid compound preferably made of tartaric acid, citric acid, boric acid or molybdic acid can remove only an ammonia component without varying a total amount of NOx or partial pressured of NO and $NO_2$. Moreover, in the NOx sensor according to the invention, only an ammonia component can be removed from the measurement gas without varying a total amount of NOx or partial pressures of NO and $NO_2$ at a position upstream of the catalyst for maintaining partial pressures of NO and $NO_2$ at constant. Therefore, it is possible to measure the NOx concentration in a highly precise manner.

BRIEF DESCRIPTION OF THE DRAWINGS

FIG. 7 is a schematic view depicting one embodiment of an apparatus for sensing low concentration NOx in which a chamber according to the invention is used;

FIGS. 8a and 8b are schematic views respectively showing one embodiment of the chamber used for the apparatus for sensing low concentration NOx shown in FIG. 7;

FIGS. 9a and 9b are schematic views respectively illustrating another embodiment of the chamber used for the apparatus for sensing low concentration NOx shown in FIG. 7;

FIG. 10 is a schematic view depicting one embodiment a gas sensor element according to the invention;

FIG. 11 is a schematic view showing a state of on oxide surface in the gas sensor element according to the invention;

FIG. 12 is a schematic view illustrating one embodiment of an ammonia removing apparatus according to the invention;

FIG. 14 is a schematic view illustrating one embodiment of an examination apparatus used in an experiment according to the invention;

FIG. 15 is a graph depicting a relation between an NOx concentration and a time in the experiment according to the invention; and FIG. 16 is a schematic view showing another embodiment of the examination apparatus used in an experiment according to the invention.

DESCRIPTION OF THE PREFERRED EMBODIMENT

Figure 1:
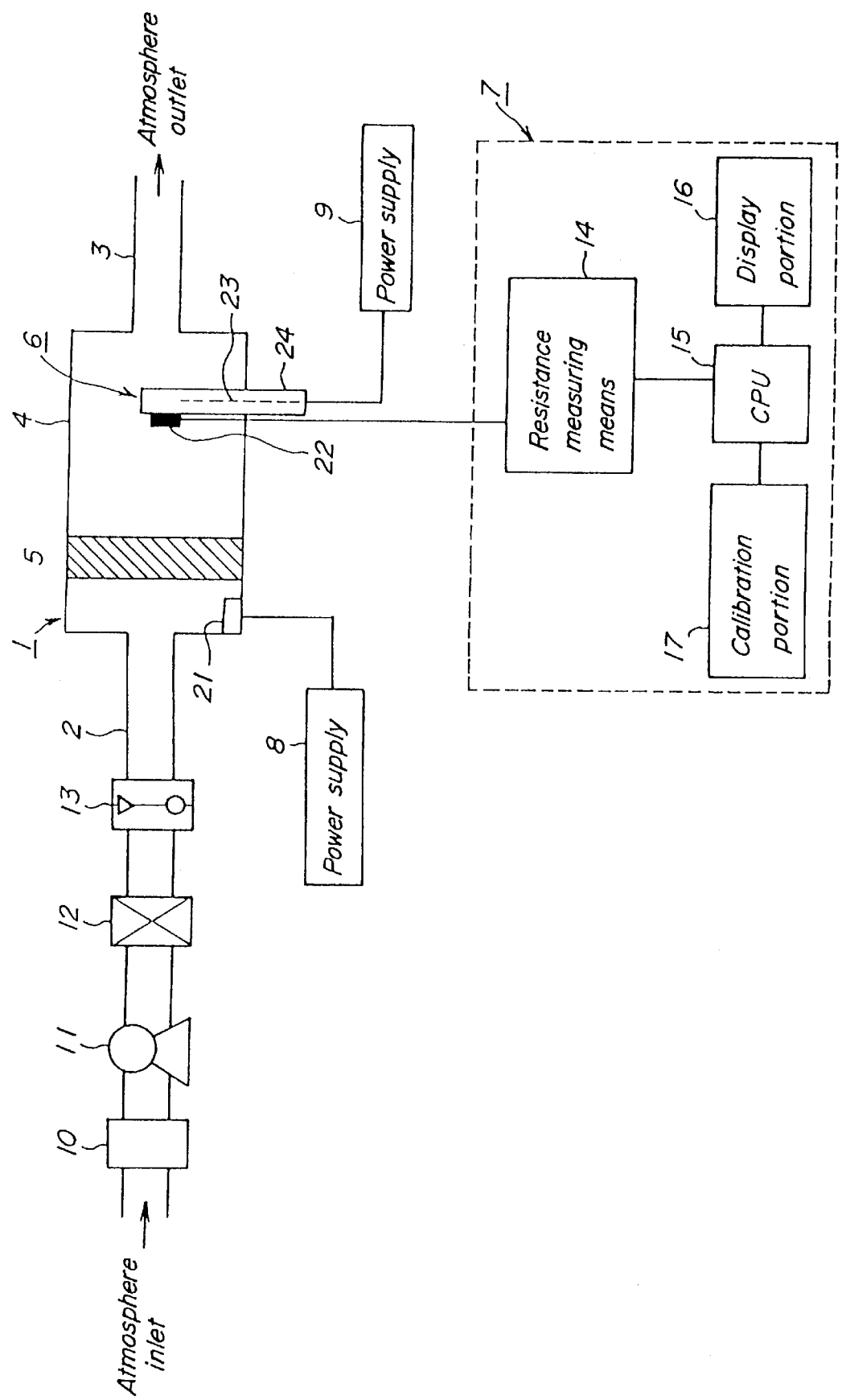
FIG. 1 is a schematic view showing one embodiment of an apparatus for sensing low concentration NOx according to a first aspect and a second aspect of the invention.

FIG. 1 is a schematic view showing one embodiment of an apparatus for sensing low concentration NOx according to the invention. The embodiment shown in FIG. 1 includes a first aspect and a second aspect of the invention. In the same manner, another embodiments shown in FIGS. 2–4 also include a first aspect and a second aspect of the invention. In the embodiment shown in FIG. 1, an apparatus for sensing low concentration NOx 1 according to the invention is constructed in such a manner that a catalyst 5 and a sensor element 6 are arranged in this order from an upstream side in a chamber 4 having an atmosphere inlet pipe 2 and an atmosphere outlet pipe 3, and a measuring portion 7 is arranged outside of the chamber 4. Moreover, a power supply 8 for heating the catalyst 5 by means of a heater 21, and a power supply 9 for heating the sensor elements 6 by means of a heater 23. In the atmosphere inlet pipe 2, there are arranged, from an upstream side of an atmosphere flow, a filter 10 for removing foreign substances, a pump 11, a pressure reducing valve 12 and a flow meter 13, so that the atmosphere is supplied in the chamber 4 always constantly. The measuring portion 7 comprises a resistance measuring means 14, a CPU 15, a display portion 16 and a calibration portion 17. In the measuring portion 7, a resistance variation of the sensor element 6 is detected, and an NOx concentration in the atmosphere is measured and displayed.

The catalyst 5 is used for maintaining partial pressures of NO and $NO_2$ in the atmosphere at an equilibrium state and for removing a combustible gas such as CO from the atmosphere by firing it. As a material of the catalyst 5, it is preferred to use a precious metal or a metal oxide. As a precious metal, it is preferred to use platinum, rhodium or gold. As a metal oxide, it is preferred to use manganese oxide, cobalt oxide or tin oxide. The catalyst 5 is heated by the heater 21 arranged in the chamber 4. Power is supplied to the heater 21 from the power supply 8.

In the sensor element 6, an oxide 22, whose resistance is varied in response to changes in NOx concentration of the atmosphere if it is contacted with the atmosphere, is arranged on a surface of a ceramic substrate 24. In this embodiment, the heater 23 is arranged in the ceramic substrate 24. Power is supplied to the heater 23 from the power supply 9. As the oxide 22, it is preferred to use a metal oxide semiconductor. As the metal oxide semiconductor, it is preferred to use $SnO_2$ or a mixture of $SnO_2$ and additives preferably consisting of Ta and Rh. If the oxide mentioned above is used for the sensor elements 6, it is possible to use the other features such as a construction and a shape, which are previously known, for the sensor element 6.

In the apparatus for sensing low concentration NOx 1, the first aspect of the invention can be achieved by removing the catalyst 5 from the construction shown in FIG. 1 and by maintaining a temperature T of the sensor element 6 in an actual use in a range of $500°$ C.$\leq T\leq 800°$ C. by means of the power supply 9 for heating the sensor element 6. Moreover, the second aspect of the invention can be achieved by arranging the catalyst 5 at a position upstream of the measurement gas flow and by maintaining a temperature T of the sensor element 6 in an actual use in a range of $500°$ C.$\leq T\leq 800°$ C. by means of the power supply 9 as is the same as the first aspect of the invention.

Hereinafter, a method of measuring an NOx concentration in the apparatus for sensing low concentration NOx 1 having the construction mentioned above according to the invention will be explained. At first, a temperature T of the sensor element 6 is controlled by the power supply 9 in a range of $500°$ C.$\leq T\leq 800°$ C. In addition, a temperature T of the catalyst 5 is controlled by the power supply 8 at a temperature of for example $380°$ C. at which the catalyst 5 can be activated. Under such a condition mentioned above, the atmosphere including NOx is supplied from the atmosphere inlet pipe 2 into the chamber 4. The thus supplied atmosphere is contacted with the catalyst 5, and partial pressures of NO and $NO_2$ i.e. $NO/NO_2$ ratio in the atmosphere is maintained at an equilibrium state. Moreover, combustible substances such as CO are removed from the atmosphere. Then, the thus prepared atmosphere, in which $NO/NO_2$ ratio is maintained at an equilibrium state, combustible substances are removed, and a temperature is maintained in a range of $500°$ C.$\leq$T$\leq 800°$ C., is contacted with the sensor element 6, and a resistance of the sensor element 6 is measured. In this case, since an oxygen concentration of the atmosphere is at constant, a variation of the measured resistance of the sensor element 6 directly corresponds to the NOx concentration. Therefore, a resistance value measured by the resistance measuring means 14 is calculated by the CPU 15 to obtain an NOx concentration, and the thus obtained NOx concentration is indicated on the display portion 16.

Figure 2:
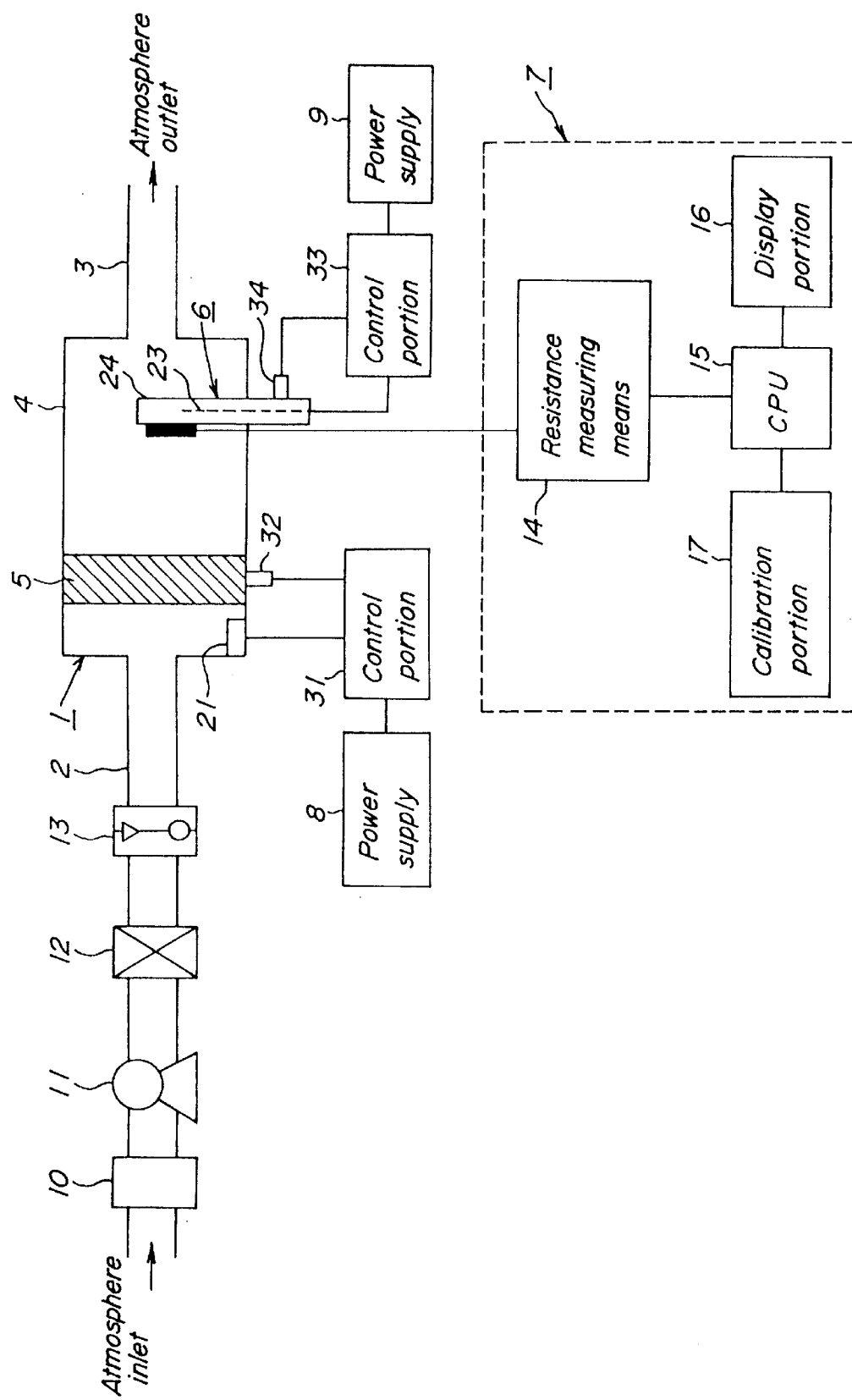
FIG. 2 is a schematic view illustrating another embodiment of the apparatus for sensing low concentration NOx according to the first aspect and the second aspect of the invention.

FIG. 2 is a schematic view showing another embodiment of an apparatus for sensing low concentration NOx according to the invention. In the embodiment shown in FIG. 2, portions similar to those of FIG. 1 are denoted by the same reference numerals used in FIG. 1, and the explanations thereof are omitted here. In the embodiment shown in FIG. 2, a different point from the embodiment shown in FIG. 1 is that temperature control means for controlling temperatures of the catalyst 5 and the sensor element 6 at constant are provided. That is to say, in order to control a temperature of the catalyst 5 at constant, a control portion 31 and a thermocouple 32 for measuring a temperature of the catalyst 5 are provided. Then, a temperature of the catalyst 5 is maintained for example in a range of $380°$ C.$\pm 0.1°$ C. by controlling on/off operation of power supplied from the power supply 8 in such a manner that time duration of on time and off time are varied, or by controlling an output amount of power supplied from the power supply 8, in the control portion 31, according to a temperature of the catalyst 5 measured by the thermocouple 32. Moreover, a control portion 33 and a thermocouple 34 are also provided in the sensor element 6, the same temperature control as that of the catalyst 5 mentioned above is performed to maintain a temperature of the sensor element 6 in a range of $500°$ C.–$800°$ C.$\pm 0.1°$ C.

In this embodiment, another method can be used for maintaining temperatures of the catalyst 5 and the sensor element 6 at constant. For example, a bridge circuit can be constructed including Pt resistor used for the heater 21 and the heater 23, and temperature control of the catalyst 5 and the sensor element 6 may be performed on the basis of a resistance variation of the Pt resistor.

Figure 3:
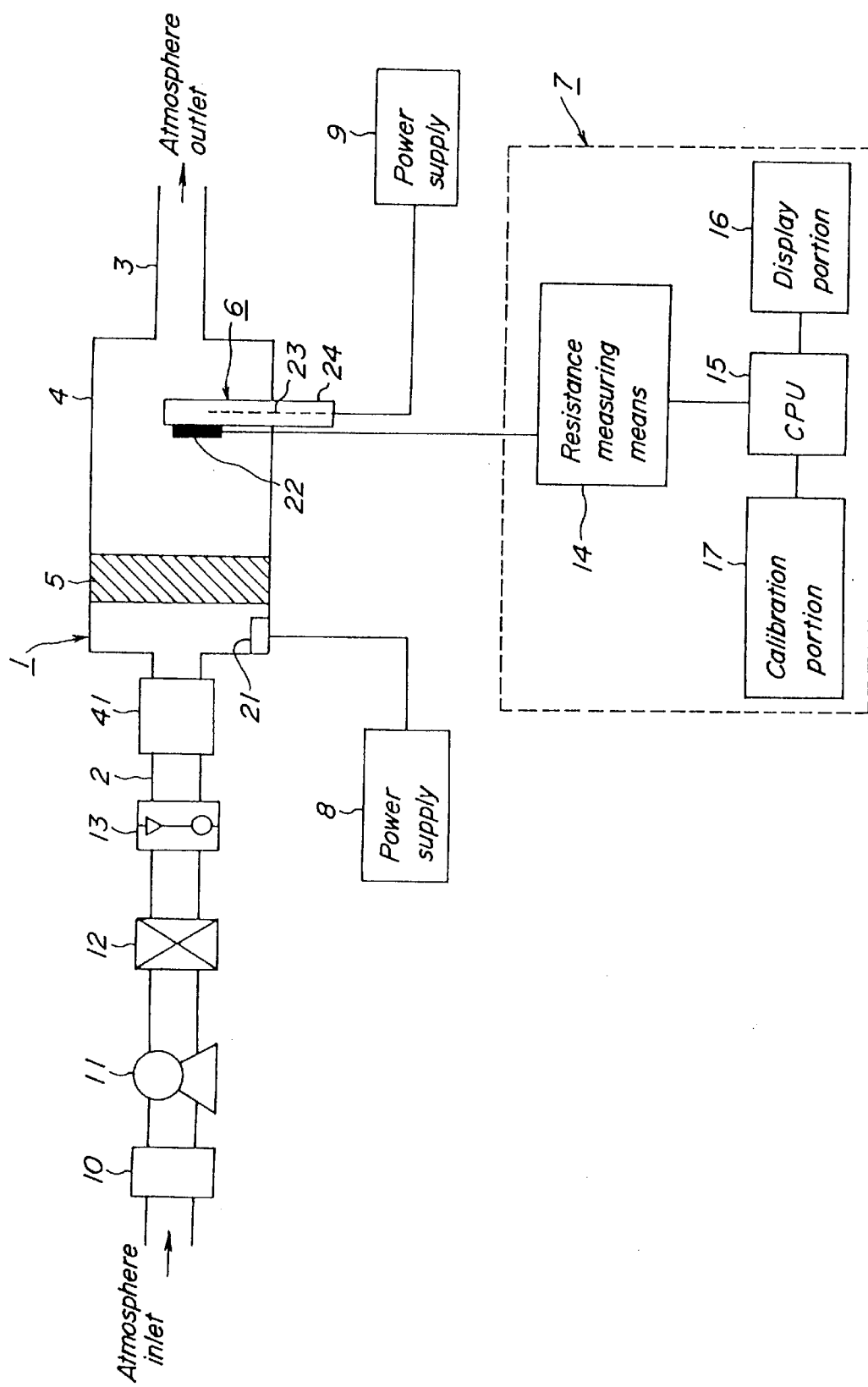
FIG. 3 is a schematic view depicting still another embodiment of the apparatus for sensing low concentration NOx according to the first and the second aspect of the invention.

FIG. 3 is a schematic view showing still another embodiment of an apparatus for sensing low concentration NOx according to the invention. In the embodiment shown in FIG. 3, portions similar to those of FIG. 1 are denoted by the same reference numerals used in FIG. 1, and the explanations thereof are omitted here. In the embodiment shown in FIG. 3, a different point from the embodiment shown in FIG. 1 is that a water control means for controlling the water component included in the atmosphere at constant is arranged upstream of the atmosphere flow as the measurement gas with respect to the sensor element 6. That is to say, a freezer 41 is arranged in the atmosphere inlet pipe 2 at a position downstream of the flow meter 13 to control a dew point of the atmosphere in a range of dew point $\pm 0.2°$ C. As the freezer 41, it is preferred to use a freezer utilizing a peltier element based on Peltier effect, but the other freezer such as Perma Pure Dryer (product name) may be used for this purpose. In order to sense low concentration NOx in a highly precise manner, it is important to keep a water component amount in the atmosphere constant, and thus it is preferred to arrange such a water component control means for controlling a water component in the atmosphere at constant.

Figure 4:
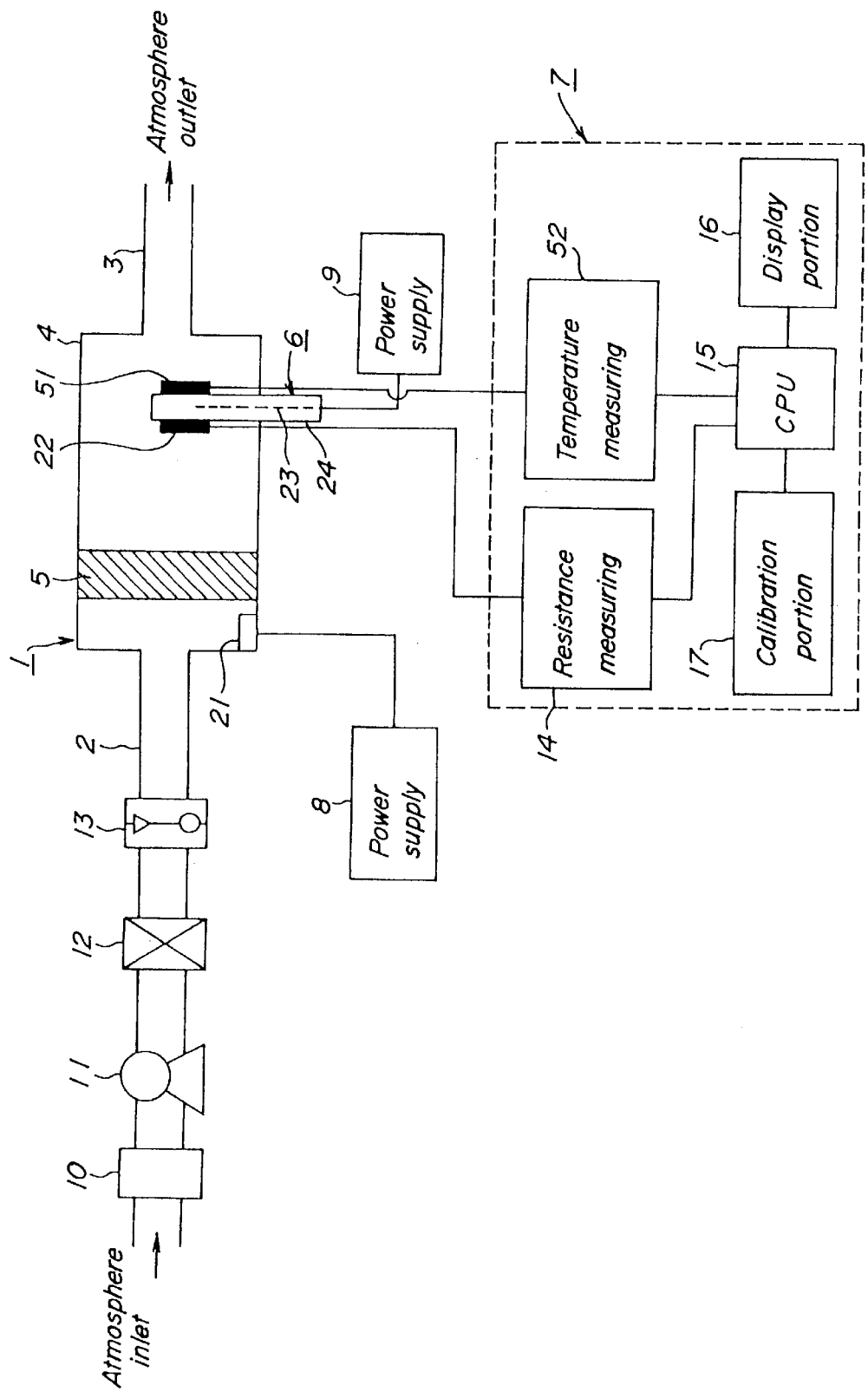
FIG. 4 is a schematic view showing still another embodiment of the apparatus for sensing low concentration NOx according to the first and the second aspect of the invention.

FIG. 4 is a schematic view showing still another embodiment of an apparatus for sensing low concentration NOx according to the invention. In the embodiment shown in FIG. 4, portions similar to those of FIG. 1 are denoted by the same reference numerals used in FIG. 1, and the explanations thereof are omitted here. In the embodiment shown in FIG. 4, the distinguishing feature from the embodiment shown in FIG. 1 is that a temperature detection means is arranged proximate the sensor element 6 so as to correct a resistance variation of the sensor element 6 due to a temperature variation. That is to say, an oxide whose resistance variation due to a temperature variation is the same as that of the sensor element 6 e.g. an oxide having the same chemical composition as that of the oxide 22 is arranged on a surface of the ceramic substrate 24 opposed to the surface to which the oxide 22 is arranged. A temperature variation of the sensor element 6 is measured by a temperature measuring portion 52 arranged in the measuring portion 7 on the basis of the resistance variation of the thus arranged oxide. It is possible to correct a resistance variation of the sensor element 6 in response to the thus measured temperature variation. In order to correct a resistance variation, the known correction method can be used. Moreover, it is possible to perform the same resistance variation correction by utilizing a thermocouple as the resistance detecting means. Further, it is possible to perform the same resistance variation correction by utilizing a resistance variation of the heater for heating the sensor element 6 as the temperature detecting means. In order to sense low concentration NOx in a highly precise manner, it is preferred to correct a resistance variation of the sensor element on the basis of a temperature variation of the sensor element as well as a water control operation.

Hereinafter, an actual experiment will be explained.

Experiment 1 (first aspect)

NOx sensors having a construction such that the catalyst 5 was removed from the construction shown in FIG. 1, in which $SnO_2$ was used for the oxide of the sensor element, were prepared. A manufacturing of the sensor element was performed as follows. At first, tin chloride was subjected to a hydrolysis by using an ammonia solution to obtain a dissolved solution. Then, the dissolved solution was separated by a filtering. After that, the thus separated dissolved solution was subjected to a pyrolysis at $600°$ C. for 2 hours to synthesize tin oxide powders. Then, the thus obtained tin oxide powders were mixed in a wet state in a mixed solution of acetone and diethylehexanol with organic binders and plasticizers for 10 hours by using zirconia balls. After that, acetone was vaporized to obtain an tin oxide slurry for a screen printing. As a substrate of the sensor element, use was made of an alumina plate having a dimension of 1×5×65 mm. Platinum electrodes and platinum heaters were previously screen-printed on the substrate, and the thus obtained tin oxide slurry was screen-printed on tip portions of the electrodes. The thus screen-printed substrate was fired at $800°$ C. for 2 hours to obtain a sensor element.

By using the thus prepared NOx sensors according to the present embodiments 1–2 and the comparative embodiments 1–2, in which a temperature of the sensor element was set as shown in the following Table 1, NOx concentrations in the measurement gas in which NOx concentrations were controlled from 1 ppb to 1000 ppb by means of a mass-flow controller under a condition of $NO/NO_2=1/1$. Calibration operation was performed previously at a temperature shown in Table for all the cases.

TABLE 1

|  | Present embodiment 1 | | Present embodiment 2 | | Comparative embodiment 1 | | Comparative embodiment 2 | |
|---|---|---|---|---|---|---|---|---|
| Element | $SnO_2$ | | $SnO_2$ | | $SnO_2$ | | $SnO_2$ | |
| Temperature | 500° C. | | 800° C. | | 400° C. | | 900° C. | |
| Concentration (ppb) | setting concentration | measured value | setting concentration | measured value | setting concentration | measured value | setting concentration | measured value |
|  | 1000 | 1020 | 1000 | 1013 | 1000 | 1100 | 1000 | 392 |
|  | 500 | 488 | 500 | 510 | 500 | 902 | 500 | 234 |
|  | 200 | 195 | 200 | 210 | 200 | 850 | 200 | 322 |
|  | 100 | 96 | 100 | 110 | 100 | 810 | 100 | 121 |
|  | 70 | 68 | 70 | 69 | 70 | 784 | 70 | 134 |
|  | 50 | 46 | 50 | 43 | 50 | 732 | 50 | 24 |
|  | 20 | 25 | 20 | 22 | 20 | 702 | 20 | 13 |
|  | 10 | 16 | 10 | 13 | 10 | 687 | 10 | 12 |
| Inclination A | 0.9999 | | 0.9999 | | 0.97 | | 0.83 | |
| Correlation coefficient r | 0.99 | | 1.01 | | 0.38 | | 0.35 | |

From the results shown in Table 1, it is confirmed that the NOx sensors according to the present embodiments 1–2 have a higher correlation between the measured value and the predetermined concentration as compared with the NOx sensors according to the comparative examples 1–2 and thus it is possible to measure a low concentration NOx in a highly precise manner. In the comparative embodiment 1 in which a temperature of the sensor element is 400° C., since NOx components are not adsorbed to the response portion at an equilibrium state, the result of the calibration operation is not maintained if a temperature varies from a temperature at which the calibration operation is performed. Therefore, it is confirmed that it is not possible to measure an NOx concentration in a precise manner. Moreover, in the comparative embodiment 2 in which a temperature of the sensor element is 900° C., a resistance variation of the sensor element with respect to a variation of an NOx concentration is extremely small, and thus it is confirmed that it is not possible to measure an NOx concentration in a precise manner.

Experiment 2 (second aspect)

NOx sensors having the construction shown in FIG. 4 according to the present embodiments 11–17 and the comparative embodiments 11–13, in which a kind of the oxide of the sensor element and a use of the catalyst are varied as shown in the following Table 2, were prepared. A manufacturing of the sensor element was performed as follows. At first, tin chloride was subjected to a hydrolysis by using an ammonia solution to obtain a dissolved solution. Then, the dissolved solution was separated by a filtering. After that, the thus separated dissolved solution was subjected to a pyrolysis at 600° C. for 2 hours to synthesize tin oxide powders. Then, the thus obtained tin oxide powders were mixed in a wet state in a mixed solution of acetone and diethylehexanol with organic binders and plasticizers for 10 hours by using zirconia balls. After that, acetone was vaporized to obtain an tin oxide slurry for a screen printing. As a substrate of the sensor element, use was made of an alumina plate having a dimension of 1×5×65 mm. Platinum electrodes and platinum heaters were previously screen-printed on the substrate, and the thus obtained tin oxide slurry was screen-printed on tip portions of the electrodes. The thus screen-printed substrate was fired at 800° C. for 2 hours to obtain a sensor element. In the case that Ta was included in the sensor element in a wet mixing operation, tantalum oxide was added with the organic binders. In this experiment, an amount of Ta was 3 at % with respect to Sn atoms. Moreover, in the case that Rh was included in the sensor element, rhodium nitrate solution was applied on the sensor element and the thus prepared sensor element was fired at 800° C. for 2 Hr.

In the thus prepared NOx sensors according to the present embodiments 11–17 and the comparative embodiments 11–13, a temperature of the sensor element, whether or not a temperature control was effected, whether or not a resistance correction was effected, and whether or not a water control was effected, were respectively set as shown in the following Tables 2 and 3. Under such a condition, an NOx concentration were measured in the manner mentioned above at arbitrary 15 points in the atmosphere, and an average value of data obtained for 1 hour was compared with a value measured according to an absorptiometry shown in JISB7953. An estimation was performed by comparing an inclination A and a correlation coefficient r of a regression curve with respect to the data measured by an absorptiometry. The results were shown in Tables 2 and Table 3.

TABLE 2(a)

|  | Present embodiment 11 | Present embodiment 12 | Present embodiment 13 | Present embodiment 14 |
|---|---|---|---|---|
| Element | $SnO_2$ | $SnO_2$ | $SnO_2$ | $SnO_2$ + Ta + Rh |
| Catalyst | Pt | Pt | Pt | Pt |
| Temperature | 520° C. | 500° C. | 800° C. | 520° C. |
| Temperature control | none | none | none | none |
| Water control | none | none | none | none |
| Resistance correction | none | none | none | none |

TABLE 2(a)-continued

|  | Present embodiment 11 | | Present embodiment 12 | | Present embodiment 13 | | Present embodiment 14 | |
| --- | --- | --- | --- | --- | --- | --- | --- | --- |
| Concentration (ppb) | absorptiometry | measured value | absorptiometry | measured value | absorptiometry | measured value | absorptiometry | measured value |
|  | 54 | 48 | 48 | 54 | 54 | 48 | 12 | 15 |
|  | 120 | 115 | 80 | 75 | 118 | 110 | 49 | 52 |
|  | 25 | 20 | 32 | 36 | 25 | 19 | 50 | 45 |
|  | 30 | 36 | 54 | 48 | 29 | 36 | 80 | 84 |
|  | 50 | 58 | 120 | 112 | 56 | 55 | 37 | 42 |
|  | 79 | 83 | 25 | 20 | 140 | 137 | 56 | 53 |
|  | 90 | 87 | 90 | 85 | 50 | 51 | 136 | 132 |
|  | 48 | 54 | 56 | 50 | 80 | 84 | 50 | 54 |
|  | 80 | 75 | 136 | 132 | 37 | 42 | 79 | 85 |
|  | 32 | 36 | 50 | 54 | 56 | 50 | 73 | 74 |
|  | 66 | 58 | 67 | 58 | 66 | 57 | 80 | 83 |
|  | 149 | 142 | 149 | 142 | 150 | 140 | 87 | 93 |
|  | 22 | 27 | 21 | 28 | 22 | 28 | 90 | 84 |
|  | 86 | 91 | 66 | 58 | 94 | 91 | 101 | 104 |
|  | 101 | 94 | 101 | 94 | 44 | 40 | 65 | 60 |
|  | 55 | 48 | 55 | 44 | 56 | 48 | 150 | 143 |
| Inclination A | 0.921 | | 0.929 | | 0.932 | | 0.947 | |
| Correlation coefficient r | 0.987 | | 0.99 | | 0.991 | | 0.992 | |

TABLE 2(b)

|  | Present embodiment 15 | | Present embodiment 16 | | Present embodiment 17 | |
| --- | --- | --- | --- | --- | --- | --- |
| Element | $SnO_2$ + Ta + Rh | | $SnO_2$ + Ta + Rh | | $SnO_2$ + Ta + Rh | |
| Catalyst | Pt | | Pt | | Pt | |
| Temperature | 520° C. | | 520° C. | | 520° C. | |
| Temperature control | effect | | effect | | effect | |
| Water control | none | | none | | effect | |
| Resistance correction | none | | effect | | effect | |
| Concentration (ppb) | absorptiometry | measured value | absorptiometry | measured value | absorptiometry | measured value |
|  | 18 | 14 | 63 | 62 | 49 | 52 |
|  | 60 | 52 | 49 | 46 | 50 | 49 |
|  | 162 | 160 | 23 | 24 | 80 | 82 |
|  | 90 | 93 | 87 | 89 | 87 | 90 |
|  | 50 | 53 | 46 | 49 | 57 | 60 |
|  | 53 | 55 | 56 | 55 | 97 | 103 |
|  | 68 | 70 | 140 | 137 | 140 | 143 |
|  | 70 | 65 | 50 | 51 | 50 | 54 |
|  | 22 | 20 | 94 | 91 | 60 | 56 |
|  | 129 | 120 | 44 | 40 | 162 | 160 |
|  | 147 | 140 | 67 | 66 | 90 | 93 |
|  | 55 | 64 | 90 | 91 | 50 | 52 |
|  | 83 | 86 | 163 | 158 | 50 | 50 |
|  | 24 | 27 | 102 | 103 | 49 | 48 |
|  | 65 | 67 | 40 | 43 | 23 | 24 |
|  | 92 | 90 | 78 | 82 | 87 | 89 |
| Inclination A | 0.957 | | 0.969 | | 1.003 | |
| Correlation coefficient r | 0.994 | | 0.998 | | 0.998 | |

TABLE 3

|  | Comparative embodiment 11 | Comparative embodiment 12 | Comparative embodiment 13 |
| --- | --- | --- | --- |
| Element | $SnO_2$ | $SnO_2$ | $SnO_2$ |
| Catalyst | none | effect | effect |
| Temperature | 520° C. | 450° C. | 850° C. |

TABLE 3-continued

| | absorp-tiometry | measured value | absorp-tiometry | measured value | absorp-tiometry | measured value |
|---|---|---|---|---|---|---|
| Temperature control | none | | none | | none | |
| Water control | none | | none | | none | |
| Resistance correction | none | | none | | none | |
| Concentration (ppb) | 39 | 62 | 50 | 56 | 68 | 40 |
| | 58 | 46 | 109 | 118 | 120 | 80 |
| | 23 | 24 | 23 | 110 | 30 | 67 |
| | 87 | 100 | 34 | 98 | 34 | 98 |
| | 57 | 70 | 56 | 90 | 69 | 21 |
| | 97 | 135 | 45 | 88 | 21 | 72 |
| | 140 | 180 | 140 | 176 | 140 | 130 |
| | 50 | 78 | 90 | 160 | 89 | 130 |
| | 33 | 91 | 94 | 155 | 57 | 80 |
| | 76 | 100 | 32 | 134 | 32 | 22 |
| | 129 | 60 | 67 | 132 | 66 | 100 |
| | 35 | 70 | 87 | 123 | 93 | 43 |
| | 50 | 33 | 162 | 200 | 178 | 100 |
| | 102 | 90 | 111 | 190 | 113 | 130 |
| | 36 | 50 | 40 | 159 | 34 | 54 |
| | 78 | 82 | 78 | 157 | 58 | 79 |
| Inclination A | 0.74 | | 0.69 | | 0.48 | |
| Correlation coefficient r | 0.68 | | 0.69 | | 0.39 | |

From the results shown in Table 2 and Table 3, it is understood that the NOx concentrations of the present embodiments 11–17 measured according to the invention are identical with those measured by an absorptiometry and thus it is possible to measure an NOx concentration in a highly precise manner. Moreover, from these results, it is understood that it is necessary to maintain a temperature T of the sensor element in a range of $500°\ C. \leq T \leq 800°\ C$. On the other hand, in the comparative embodiment 1 in which no catalyst is used, it is understood that, if a temperature T of the sensor element satisfies the range of $500°\ C. \leq T \leq 800°\ C.$, the measured NOx concentration is not identical with that measured by an absorptiometry. Further, in the comparative embodiments 12 and 13 in which a temperature T of the sensor element is out of the range of $500°\ C. T \leq 800°\ C.$, it is understood that, even if the catalyst is used, the measured NOx concentration is not identical with that measured by an absorptiometry. In addition, it is understood that, if compared the data of the present embodiments 14–17, the embodiments 15–17, to which a temperature control and/or a resistance correction and/or a water control are effected, can obtain more precise NOx concentration as compared with the embodiment 14, to which no temperature control, resistance correction, water control are effected.

Figure 5:
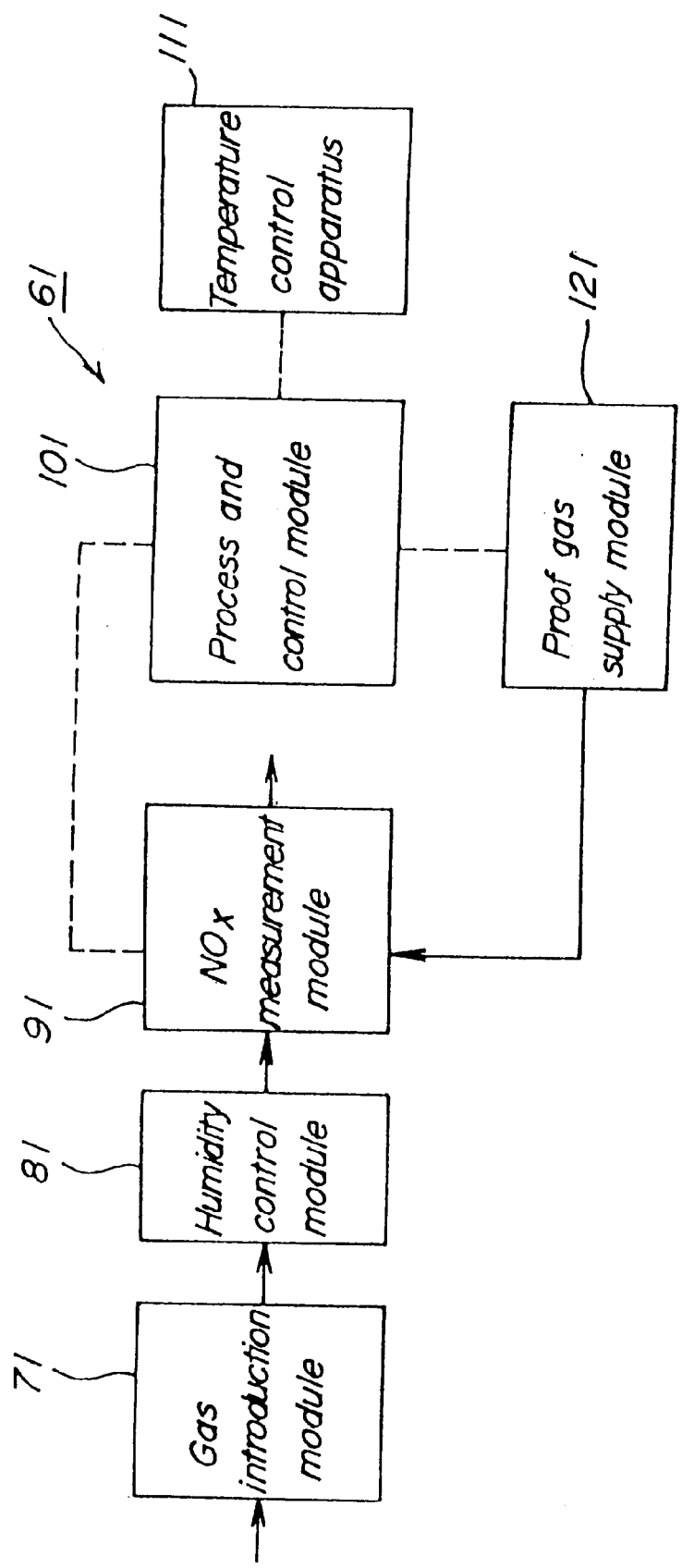
FIG. 5 is a schematic view illustrating one embodiment of an apparatus for sensing low concentration NOx according to a third aspect of the invention.

FIG. 5 is a schematic view showing one embodiment of an apparatus according to the third aspect of the invention. In the embodiment shown in FIG. 5, an apparatus for sensing low concentration NOx 61 comprises: a gas introduction module 71 for introducing the measurement gas therein from the outside; a humidity control module 81 for controlling a humidity of the measurement gas introduced by the gas introduction module 71; an NOx measurement module 91 for measuring an NOx concentration in the measurement gas in which humidity is controlled by the humidity control module 81, comprising a sensor element made of a metal oxide semiconductor arranged in a flow path of the measurement gas, the resistance of the sensor element varying in response to changes in NOx concentration in the measurement gas; and a process and control module 101 for calculating an NOx concentration on the basis of a resistance value measured by the sensor element of the NOx measurement module 91 and for controlling the humidity control module 81 and the NOx measurement module 91. Moreover, the apparatus for sensing low concentration NOx 61 shown in FIG. 5 further comprises: a temperature control apparatus 111 for maintaining a temperature surrounding the apparatus; and a proof gas supply module 121 for supplying a proof gas used for proofreading the sensor element of the NOx measurement module 91. The temperature control apparatus 111 and the proof gas supply module 121 may be arranged as need.

In the apparatus for sensing low concentration NOx 61 shown in FIG. 5, the atmosphere as the measurement gas is introduced into the apparatus through the gas introduction module 71. Then, the thus introduced atmosphere is supplied to the humidity control module 81 to control a humidity of the atmosphere. Then, the thus humidity controlled atmosphere is supplied to the NOx measurement module 91. In the NOx measurement module 91, there is arranged the sensor element made of a metal oxide semiconductor, the resistance of the sensor element varying in response to changes in NOx concentration in the atmosphere if it is contacted with the atmosphere including NOx. Therefore, it is possible to measure a resistance of the sensor element in response to an NOx concentration in the atmosphere. The thus measured resistance of the sensor element is supplied to the process and control module 101. In the process and control module 101, an NOx concentration, or respective NO concentration and $NO_2$ concentration if the sensor element construction is different, can be measured from the thus supplied resistance on the basis of a predetermined relation between resistance and NOx concentration. Since the above relation between resistance and NOx concentration is varied in this NOx sensor if a time elapses, it is necessary to correct an output of the sensor element by using the proof gas supply module 121. Moreover, the temperature control apparatus 111 is used for maintaining a temperature surrounding the apparatus at constant.

In the apparatus for sensing low concentration NOx 61 having the construction shown in FIG. 5, the NOx measurement module 91 having the sensor element made of a metal oxide semiconductor, which is known as effective for an NOx concentration measurement in the combusted exhaust gas, is combined with the best tuned gas introduction module 71, humidity control module 81, and process and control module 101. Therefore, it is possible to measure an NOx concentration in the measurement gas such as the atmosphere including low concentration NOx in a highly precise manner.

Figure 6:
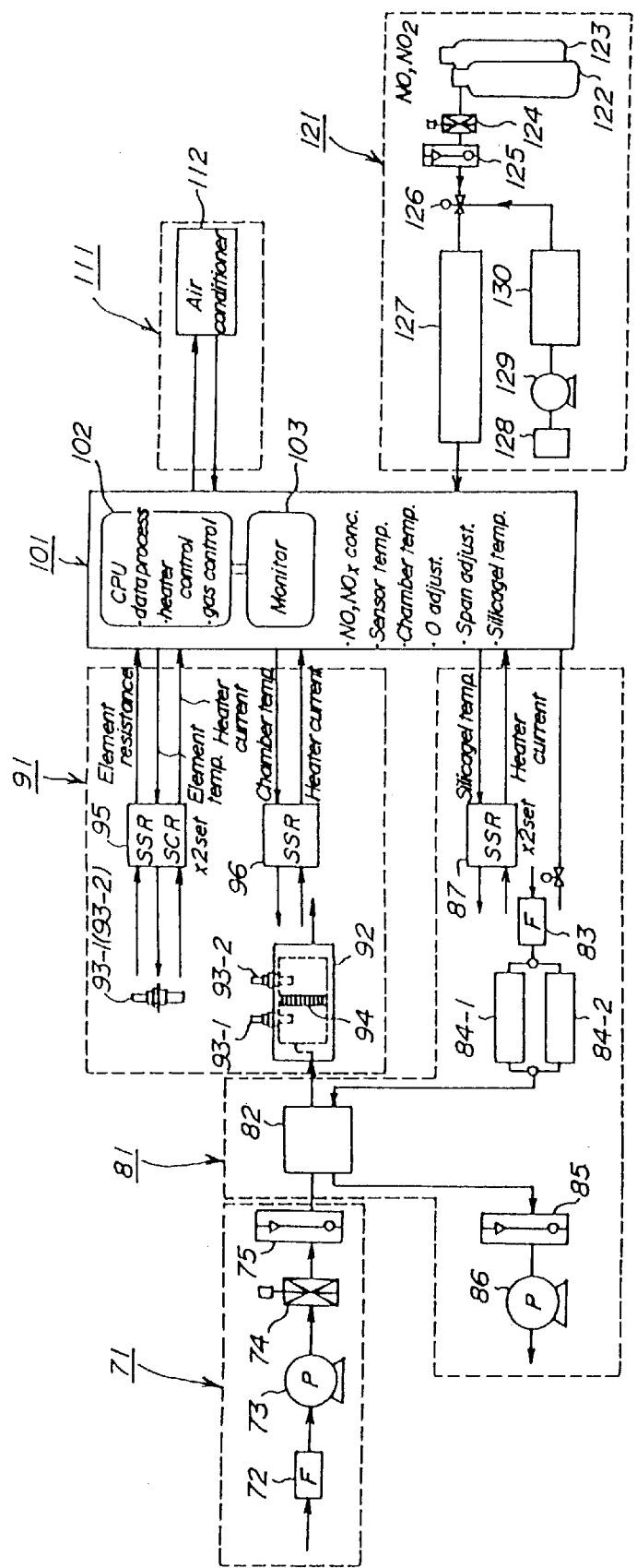
FIG. 6 is a schematic view for explaining in detail the apparatus for sensing low concentration NOx shown in FIG. 5.

FIG. 6 is a schematic view showing a detail construction of the apparatus for sensing low concentration NOx shown in FIG. 5. In the embodiment shown in FIG. 6, portions similar to those of FIG. 5 are denoted by the same reference numerals shown in FIG. 5, and the explanations thereof are omitted here. In the embodiment shown in FIG. 6, the gas introduction module 71 comprises: from an upstream side of the atmosphere flow, a dust filter 72; a pump 73; a pressure reducing pump 74; and a flow meter 75 so as to supply a constant amount of the atmosphere as the measurement gas always constantly. As the dust filter 72, use is made of the dust filter which can remove dusts having a particle size of larger than for example 0.5 $\mu$m. As the pump 73, use is made of the pump having an efficiency such that a flow amount of the atmosphere per 1 minute can be controlled as 1–3 litters. In this embodiment, a flow amount of the atmosphere passing through the flow meter 75 is controlled to be 200 cc per minute at most, preferably 10 cc per minute.

The humidity control module 81 mainly comprises a Perma Pure Dryer 82 (product name) as a humidity control apparatus, and, in order to supply the atmosphere for a humidity control to the Perma Pure Dryer 82, it further comprises a filter 83, a pair of dryers 84-1 and 84-2, a flow meter 85, and a pum 86. Moreover, a thermometer and a heater are arranged respectively to the dryers 84-1 and 84-2, and temperatures of the dryers 84-1 and 84-2 are controlled by a control portion 87 under a control of the process and control module 101. The reason for arranging a pair of the dryers is that an NOx concentration measurement can be performed continuously. That is to say, when one dryer is used, the other dryer us regenerated by heating and drying silica gel. A control of this operation is also performed by the process and control module 101. In the humidity control module 81, it is preferred to maintain a humidity in a range of 0.1%±0.005% by controlling a dew point of for example in a range of dew point (−20° C.±0.2° C. As one example, a flow rate of the atmosphere supplying to the Perma Pure Dryer 82 by means of the filter 83, the dryers 84-1, 84-2, the flow meter 85, and the pump 86 is 500 cc/minute. In order to measure low concentration NOx in the atmosphere in a highly precise manner, it is important to maintain a water component in the atmosphere at constant, and thus in this embodiment, use is made of the humidity control module 81.

The NOx measurement module 91 comprises, in a chamber 12, a sensor element 93-1, a catalyst 94, and a sensor element 93-2, from an upstream side of the atmosphere flow. Respective sensor elements 93-1 and 93-2 are connected to the process and control module 101 so as to supply data measured by the respective sensor elements 93-1, 93-2 to the process and control module 101. A thermometer and a heater are arranged respectively to the sensor elements 93-1 and 93-2, and temperatures of respective sensor elements 93-1 and 93-2 are controlled by a control portion 95 under a control of the process and control module 101. In the same manner, a thermometer and a heater are arranged respectively to the chamber 92, and a temperature of the catalyst 94 is controlled by a control portion 96 under a control of the process and control module 101.

Moreover, in the case that resistances of the sensor elements 93-1 and 93-2 are varied in response not only to changes in an NOx concentration but also to changes in a small amount of ammonia gas existent in the atmosphere, it is preferred to remove an ammonia component by means of an ammonia removing module (not shown). The ammonia removing module has a filter, in which powders of organic acid such as citric acid and oxalic acid or inorganic acid such as boric acid and phosphoric acid are filled, so as to react and remove an ammonia component as a salt form. Further, in the case that resistances of the sensor elements 93-1 and 93-2 are varied in response not only to changes in an NOx concentration but also to changes in a small amount of ozone gas existent in the atmosphere, it is preferred to remove an ozone component by means of an ozone removing module (not shown). The ozone removing module has for example a calorite known as an ozone dissolving catalyst, so as to dissolve and remove an ozone component as an oxygen form.

The catalyst 94 is used for maintaining partial pressures of NO and $NO_2$ in the atmosphere at an equilibrium state and for removing a combustible gas such as CO from the atmosphere by firing it. As a material of the catalyst 94, it is preferred to use a precious metal or a metal oxide. As a precious metal, it is preferred to use platinum, rhodium or gold. As a metal oxide, it is preferred to use manganese oxide, cobalt oxide or tin oxide. In the sensor element 93-1 or 93-2, an oxide, whose resistance is varied in response to changes in NOx concentration of the atmosphere if it is contacted with the atmosphere, is arranged on a surface of a ceramic substrate. In this embodiment, the heater heated by the control portion 95 under a control of the process and control module 101. As the oxide mentioned above, it is preferred to use a metal oxide semiconductor. As the metal oxide semiconductor, it is preferred to use $SnO_2$ or a mixture of $SnO_2$ and additives preferably consisting of Ta and Rh. Each of the sensor elements 93-1 and 93-2 has the same construction with each other. If the oxide mentioned above is used for the sensor elements 93-1 and 93-2, it is possible to use the other features such as a construction and a shape, which are previously known, for the sensor elements 93-1 and 93-2.

Hereinafter, a method of measuring an NOx concentration in the atmosphere for sensing low concentration NOx having the construction mentioned above according to the invention will be explained. At first, temperatures T of the sensor elements 93-1 and 93-2 are respectively controlled by the control portion 95 preferably in a range of 500° C.$\leq$T$\leq$800° C. In addition, a temperature of the catalyst 94 is controlled by the control portion 96 at a temperature of for example 380° C. at which the catalyst 94 can be activated. Under such a condition mentioned above, the atmosphere including NOx is supplied into the chamber 92. The thus supplied atmosphere is contacted with the sensor element 93-1 at first, and a resistance of the sensor element 93-1 is measured. Then, the atmosphere is passed through the catalyst 94, and partial pressures of NO and $NO_2$ i.e. $NO/NO_2$ ratio in the atmosphere is maintained at an equilibrium state. Moreover, combustible substances such as CO is removed from the atmosphere. Then, the thus prepared atmosphere, in which $NO/NO_2$ ratio is maintained at an equilibrium state and combustible substances are removed, is contacted with the sensor element 93-2, and a resistance of the sensor element 93-2 is measured. A method of determining an NO concentration and an $NO_2$ concentration from the resistances of the atmosphere before and after passing through the catalyst 94 which are measured by the sensor elements 93-1 and 93-2 is as follows. Since an $NO/NO_2$ ratio of the atmosphere passing through the catalyst 94 is maintained at an equilibrium state and an NOx partial pressure is a sum of an NO partial pressure and an $NO_2$ partial pressure, the following formulas (1) and (2) can be obtained.

$$P_{NO}/P_{NO2} = \alpha \quad (1)$$

$$P_{NO} + P_{NO2} = P_{NOX} \quad (2)$$

Moreover, as the applicant is previously disclosed, a relation between a resistance R and respective partial pressures of NO, $NO_2$ and $O_2$ can be obtained as the following formula (3).

$$\frac{1}{R} = Q - \frac{AP_{NO2} + BP_{NO} + CP_{O2}^{1/2} + DP_{NO}P_{O2}^{1/2}}{1 + EP_{NO2} + FP_{NO} + GP_{O2}^{1/2} + HP_{NO}P_{O2}^{1/2}} \quad (3)$$

wherein, R: resistance, and
A–H and Q: constant.

In this case, since a partial pressure of $O_2$ ($P_{O2}$) in the atmosphere is constant, it is possible to obtain a partial pressure of NOx ($P_{NOx}$) from the resistance R measured by the sensor element 93-2 on the basis of the formulas (1)–(3) mentioned above. In the above formula (3), coefficients A–H and Q are previously determined for the sensor element 93-2 by using a gas in which NO, $NO_2$ and $O_2$ concentrations are known.

Further, it is possible to obtain a relation between a partial pressure of NO ($P_{NO}$) and a partial pressure of $NO_2$ ($P_{NO2}$) for the sensor element 6-1 from the above formula (3) by using the resistance R measured by the sensor element 93-1 for the atmosphere not passing through the catalyst 94 in which an NO/$NO_2$ ratio is varied. Also in this embodiment, coefficients A–H and Q of the formula (3) are previously determined for the sensor element 93-1 apart from those for the sensor element 93-2 by using a gas in which NO, $NO_2$ and $O_2$ concentrations are known. By solving a simultaneous equations between the thus obtained relation of $P_{NO}$ and $P_{NO2}$ for the sensor element 93-1 and the above relation of the formula (2) for the sensor element 93-2 (here, $P_{NOX}$ is known), it is possible to obtain an NO concentration and an $NO_2$ concentration respectively. In this case, since $P_{NO}$ and $P_{NO2}$ are directly corresponding to an NO concentration and an $NO_2$ concentration on the basis of previously prepared look-up tables showing a relation between $P_{NO}$ and an NO concentration and a relation between $P_{NO2}$ and an $NO_2$ concentration.

The process and control module 101 is used for performing the above mentioned process and control, and it has a CPU 102 having a memory and a monitor 103 for indicating process and control results in the CPU 102 i.e. measured results such as NOx concentration, NO concentration, $NO_2$ concentration, sensor element temperature, and a chamber temperature. Moreover, in the case that use is made of the temperature control apparatus 111 and the proof gas supply module 121, the process and control module 101 controls the temperature control apparatus 111 and the proof gas supply module 121.

The temperature control apparatus 111 comprises an air conditioner 112 that controls a temperature surrounding the apparatus from being extremely high or low i.e. at constant. The proof gas supply module 121 comprises an NO tank 122, an $NO_2$ tank 123, a pressure reducing valve 124, a flow meter 125, a switching valve 126, a mass-flow controller 127, a filter 128, a pum-p 129, and a dryer 130. A proof gas as a reference is supplied to the NOx measurement module 91, and a zero adjustment and a span adjustment are performed.

FIG. 7 is a schematic view showing one embodiment of an apparatus for sensing low concentration NOx in which a chamber according to the invention is used. In the embodiment shown in FIG. 7, a chamber construction is simplified for a convenience of explanation. In the embodiment shown in FIG. 7, an apparatus for sensing low concentration NOx 141 is constructed in such a manner that a first sensor element 146-1, a catalyst 145 and a second sensor element 146-2 are arranged in this order from an upstream side in a chamber 144 having an atmosphere inlet pipe 142 and an atmosphere outlet pipe 143, and a measuring portion 147 is arranged outside of the chamber 144. Moreover, a numeral 148 is a power supply for heating the catalyst 145 by means of a heater 161, and numerals 149-1 and 149-2 are power supplies for heating the first and second sensor elements 146-1 and 146-2 respectively by means of heaters 163-1 and 163-2. In the atmosphere inlet pipe 142, there are arranged, from an upstream side of an atmosphere flow, a filter 150 for removing foreign substances, a pump 151, a pressure reducing valve 152 and a flow meter 153, so that the atmosphere supplied in the chamber 144 is always constant.

The measuring portion 147 comprises resistance measuring means 154-1 and 154-2 arranged correspondingly to the first and second sensor elements 146-1 and 146-2, a CPU 155, a display portion 156 and a calibration portion 157. In the measuring portion 147, resistance variations of the first and second sensor elements 146-1 and 146-2 are detected, and NO concentration and $NO_2$ concentration in the atmosphere are measured respectively by using a predetermined formula mentioned below on the basis of the thus detected resistance variations before and after passing the catalyst 145. In addition, NOx concentration can be obtained from a sum of the thus measured NO concentration and $NO_2$ concentration.

The catalyst 145 is used for maintaining partial pressures of NO and $NO_2$ in the atmosphere at an equilibrium state and for removing a combustible gas such as CO from the atmosphere by firing it. As a material of the catalyst 145, it is preferred to use a precious metal or a metal oxide. As a precious metal, it is preferred to use platinum, rhodium or gold. As a metal oxide, it is preferred to use manganese oxide, cobalt oxide or tin oxide. The catalyst 145 is heated by the heater 161 arranged in the chamber 144. Power is supplied to the heater 161 from the power supply 148.

In the first sensor element 146-1 or the second sensor element 146-2, oxide 162-1 or 162-2, (whose resistance is varied in response to changes in NOx concentration of the atmosphere if it is contacted with the atmosphere,) is arranged on a surface of a ceramic substrate 164-1 or 164-2. In this embodiment, the heater 163-1 or 163-2 is arranged in the ceramic substrate 164-1 or 164-2. Power is supplied to the heater 163-1 or 163-2 from the power supply 149-1 or 149-2. As the oxide 162-1 or 162-2, it is preferred to use a metal oxide semiconductor. As the metal oxide semiconductor, it is preferred to use $SnO_2$ or a mixture of $SnO_2$ and additives preferably consisting of Ta and Rh. Each of the first sensor element 146-1 and the second sensor element 146-2 has the same construction with each other. If the oxide mentioned above is used for the first and second sensor elements 146-1 and 146-2, it is possible to use the other features such as a construction and a shape, which are previously known, for the first and second sensor elements 146-1 and 146-2.

Hereinafter, a method of measuring an NOx concentration in the atmosphere for sensing low concentration NOx having the construction mentioned above according to the invention will be explained. At first, temperatures T of the first and second sensor elements 146-1 and 146-2 are respectively controlled by the power supplies 149-1 and 149-2 preferably in a range of 500° C.≦T≦800° C. In addition, a temperature of the catalyst 145 is controlled by the power supply 148 at a temperature of for example 380° C. at which the catalyst 145 can be activated. Under such a condition mentioned above, the atmosphere including NOx is supplied from the atmosphere inlet pipe 142 into the chamber 144. The thus supplied atmosphere is contacted with the first sensor element 146-1 at first, and a resistance of the first sensor element 146-1 is measured. Then, the atmosphere is passed through the catalyst 145, and partial pressures of NO and $NO_2$ i.e. $NO/NO_2$ ratio in the atmosphere is maintained at an equilibrium state. Moreover, combustible substances such as CO are removed from the atmosphere. Then, the thus prepared atmosphere, in which $NO/NO_2$ ratio is maintained at an equilibrium state and combustible substances are removed, is contacted with the second sensor element 146-2, and a resistance of the second sensor element 146-2 is measured. A method of determining an NO concentration and an $NO_2$ concentration from the resistances of the atmosphere before and after passing through the catalyst 145 which are measured by the first and second sensor elements 146-1 and 146-2 is as follows.

Since an $NO/NO_2$ ratio of the atmosphere passing through the catalyst 145 is maintained at an equilibrium state and an NOx partial pressure is a sum of an NO partial pressure and an $NO_2$ partial pressure, the following formulas (1) and (2) can be obtained.

$$P_{NO}/P_{NO2} = \alpha \quad (1)$$

$$P_{NO} + P_{NO2} = P_{NOX} \quad (2)$$

Moreover, as the applicant is previously disclosed, a relation between a resistance R and respective partial pressures of NO, $NO_2$ and $O_2$ can be obtained as the following formula (3).

$$\frac{1}{R} = Q - \frac{AP_{NO2} + BP_{NO} + CP_{O2}^{1/2} + DP_{NO}P_{O2}^{1/2}}{1 + EP_{NO2} + FP_{NO} + GP_{O2}^{1/2} + HP_{NO}P_{O2}^{1/2}} \quad (3)$$

wherein, R: resistance, and
A–H and Q: constant.

In this case, since a partial pressure of $O_2$ ($P_{O2}$) in the atmosphere is constant, it is possible to obtain a partial pressure of NOx ($P_{NOx}$) from the resistance R measured by the second sensor element 146-2 on the basis of the formulas (1)–(3) mentioned above. In the above formula (3), coefficients A–H and Q are previously determined for the second sensor element 146-2 by using a gas in which NO, $NO_2$ and $O_2$ concentrations are known.

Further, it is possible to obtain a relation between a partial pressure of NO ($P_{NO}$) and a partial pressure of $NO_2$ ($P_{NO2}$) for the first sensor element 146-1 from the above formula (3) by using the resistance R measured by the first sensor element 146-1 for the atmosphere not passing through the catalyst 145 in which an $NO/NO_2$ ratio is varied. Also in this embodiment, coefficients A–H and Q of the formula (3) are previously determined for the first sensor element 146-1 apart from those for the second sensor element 146-2 by using a gas in which NO, $NO_2$ and $O_2$ concentrations are known. By solving a simultaneous equations between the thus obtained relation of $P_{NO}$ and $P_{NO2}$ for the first sensor element 146-1 and the above relation of the formula (2) for the second sensor element 146-2 (here, $P_{NOx}$ is known), it is possible to obtain an NO concentration and an $NO_2$ concentration respectively. In this case, since $P_{NO}$ and $P_{NO2}$ are directly corresponding to an NO concentration and an $NO_2$ concentration on the basis of previously prepared look-up tables showing a relation between $P_{NO}$ and an NO concentration and a relation between $P_{NO2}$ and an $NO_2$ concentration.

FIG. 8a is a plan view showing one embodiment of the chamber 144 of the apparatus for sensing low concentration NOx shown in FIG. 7, and FIG. 8b is a partial cross sectional view cut along A—A line in FIG. 8a. As mentioned above, the chamber 144 according to the invention shown in FIGS. 8a and 8b is used for arranging integrally the first sensor element 146-1, the catalyst 145, and the second sensor element 146-2. In the embodiment shown in FIGS. 8a and 8b, the chamber 144 is constructed in such a manner that a first sensor element securing portion 174 for securing the first sensor element 146-1, a catalyst accommodating portion 175 for accommodating the catalyst 145, and a second sensor element securing portion 176 for securing the second sensor element 146-2 are arranged in this order from an upstream side in a chamber main body 173 having a gas inlet 171 and a gas outlet 172. Moreover, shapes of the first sensor element 146-1 and the second sensor element 146-2 are planar as mentioned above, and overall portions of them are covered with a cover meter, in the embodiment shown in FIG. 8.

Moreover, the gas inlet 171 and the first sensor element securing portion 174 are communicated by a first through hole 177. The first through hole 177 is extended horizontally from the gas inlet 171 and is connected to a side wall of the first sensor element securing portion 174. The first sensor element securing portion 174 and the catalyst accommodating portion 175 are communicated by a second through hole 178. In this case, a sectional area of the second through hole 178 is smaller than that of the first sensor element securing portion 174. The second through hole 178 is extended vertically downward from a bottom wall of the first sensor element securing portion 174 and then extended horizontally, and is connected to an inlet side wall of the catalyst accommodating portion 175. The catalyst accommodating portion 175 and the second sensor element securing portion 176 are communicated by a third through hole 179. The third through hole 179 is extended vertically upward from an outlet upper wall of the catalyst accommodating portion 175 and then extended horizontally, and is connected to a side wall of the second sensor element securing portion 176. The second sensor element securing portion 176 and the gas outlet 172 are communicated by a fourth through hole 180. The fourth through hole 180 is extended vertically downward from a bottom wall of the second sensor element securing portion 176, extended horizontally, and then extended vertically upward, and is connected to the gas outlet 172.

In the embodiment shown in FIGS. 8a and 8b, covers 181-1, 181-2 are arranged respectively at tip portions of the first sensor element 146-1 and the second sensor element 146-2. As mentioned above, shapes of the first sensor element 146-1 and the second sensor element 146-2 are planar. In this embodiment, the first sensor element 146-1 and the second sensor element 146-2 are arranged in the covers 181-1, 181-2 in such a manner that metal oxide semiconductors of them are opposed respectively to holes 182-1, 182-2 arranged at side surfaces of the covers 181-1, 181-2. Moreover, holes are formed respectively at tip portions of the covers 181-1, 181-2.

In the embodiment shown in FIGS. 8a and 8b, a gas regulator 183 for the measurement gas is arranged upstream of the catalyst accommodating portion 175, and stick-shaped heaters 184-1 to 184-6 are arranged in the chamber main body at six positions shown in FIG. 8a. The gas regulator 183 is arranged to regulate a flow of the measurement gas supplied from the second through hole 178 to the catalyst accommodating portion 175 and to flow the measurement gas in a uniform manner with respect to the catalyst 145. This is because, when the catalyst 145 has a construction such that a catalyst material is supported on a honeycomb structural body, it is necessary to flow the measurement gas in a uniform manner along flow paths of the honeycomb structural body. Moreover, in this embodiment, the catalyst accommodating portion 175 has first to third accommodating portions 175-1 to 175-3, diameters of them being gradually smaller in a stepwise manner from an outer surface of the chamber 144. In this case, the catalyst 145 supported by a holder 185 is accommodated in the third accommodating portion 175-3 having a smallest diameter. The gas regulator 183 is accommodated in the second accommodating portion 175-2 to which the second through hole 178 is communicated. A cap portion 186 is accommodated in the first accommodating portion 175-1 by screwing it therein. Therefore, the catalyst 145 can be detached. Seal portions 187-1 and 187-2 are arranged to a step portion between the third accommodating portion 175-1 and the second accommodating portion 175-2 and a step portion between the second accommodating portion 175-2 and the first accommodating portion 175-1 respectively, so as to eliminate a gas inclusion from the outside.

Moreover, the stick-shaped heaters 184-1 to 185-6 are used for controlling a temperature of the catalyst 145 at constant for example at 380° C. in this embodiment by heating the chamber main body 173 in a uniform manner. In this embodiment, it is necessary to keep temperatures of the first sensor element 146-1 and the second sensor element 146-2 for example at 520° C. Therefore, the above temperature control is performed not only by the stick-shaped heaters 183-1 and 183-6 but also by heaters arranged respectively in the first sensor element 146-1 and the second sensor element 146-2. In this embodiment, a numeral 188 is a heat insulation member for keeping a temperature of the chamber main body 173, and a numeral 189 is a hole for inserting a thermometer arranged in the chamber main body 173. Moreover, in this case, the stick-shaped heaters are arranged in the chamber main body, but it is possible to use other-shaped heater instead of the stick-shaped heater. Further, in this case, the heater is arranged in the chamber main body for performing a direct heating, but it is possible to perform an indirect heat from the outside.

FIG. 9a is a plan view showing another embodiment of the chamber according to the invention, and FIG. 9b is a partial cross sectional view cut along A—A line in FIG. 9a. The embodiment shown in FIGS. 9a and 9b is preferred in the case that a resistance variation of the sensor element is affected by an ammonia component or an ozone component. In the embodiment shown in FIGS. 9a and 9b, an accommodating portion 191 is arranged in the first through hole 188 in the similar manner as that of the catalyst accommodating portion 175. In the accommodating portion 191, an ammonia removing portion 192 or an ozone removing portion 192 is arranged together with a regulator 193 and a cap portion 194. The regulator 193 and the cap portion 194 have the same construction as those of the regulator 183 and the cap portion 186. In FIGS. 9a and 9b, portions similar to those of FIGS. 8a and 8b are denoted by the same reference numerals as those of FIGS. 9a and 9b, and the explanations thereof are omitted here. In the embodiment shown in FIGS. 9a and 9b, since the ammonia removing portion 192 and the ozone removing portion 192 is added to the construction shown in FIGS. 8a and 8b, further stick-shaped heaters 184-7 and 184-8 are arranged. Moreover, since the accommodating portion 191 is one, one of the ammonia removing portion 192 and the ozone removing portion 192 is arranged as needed. However, if necessary, two accommodating portions are arranged, and both of the ammonia removing portion and the ozone removing portion may be arranged.

In the case that resistances of the sensor elements 146-1 and 146-2 are varied in response to changes in an NOx concentration, and further they are also varied with respect to a small amount of ammonia gas existent in the atmosphere, it is preferred to perform previously the ammonia removing treatment. In the embodiment shown in FIGS. 9a and 9b, in order to perform the ammonia removing operation, the ammonia removing portion 192 is formed by a filter in which powders of organic acid such as citric acid and oxalic acid or inorganic acid such as boric acid and phosphoric acid are filled, so as to react and remove an ammonia component as a salt form. Further, in the case that resistances of the sensor elements 146-1 and 146-2 are varied in response not only to changes in an NOx concentration but also to changes in a small amount of ozone gas existent in the atmosphere, it is preferred to remove an ozone component first. In the embodiment shown in FIGS. 9a and 9b, the ozone removing portion 192 made of a calorite known as an ozone dissolving catalyst is arranged so as to dissolve and remove an ozone component as an oxygen form.

FIG. 10 is a schematic view showing one embodiment of a gas sensor element according to the invention. In the embodiment shown in FIG. 10, a gas sensor element 201 is formed by arranging electric wires 203 and 204 made of a precious metal respectively at both ends of a stick-shaped insulation substrate 202, dipping the insulation substrate with the electric wires 203 and 204 in an oxide solution made of $SnO_2$ in which 1–10 atomic % of Ta is preferably dissolved in a solid-solution state to obtain an oxide layer 205 including a predetermined amount of Ta, and firing the insulation substrate with the electric wires 203 and 204 on which the oxide layer 205 is arranged. In the thus obtained gas sensor element 201, 1–10 atomic % of Ta is included in the oxide layer 205 with respect to metal atoms in the oxide layer 205. If the above mentioned gas sensor element 1 obtained is used for an NOx concentration measurement, it is possible to reduce an interference of SOx, HC, CO gases in the case of the NOx concentration measurement.

Moreover, in the case that RH is further supported in the gas sensor element 201 in which 1–10 atomic % of Ta is included in the oxide layer 205 with respect to metal atoms in the oxide layer 205, the gas sensor element 201 can be obtained as follows. At first, the gas sensor element 201, in which 1–10 atomic % of Ta is included in the oxide layer 205 with respect to metal atoms in the oxide layer 205, is prepared according to the above mentioned method. Then, a solution including Rh in such a manner that an Rh volume concentration is controlled preferably in a range from 1 ppm to 1% is immersed into the thus prepared gas sensor element 201. Then the thus solution immersed gas sensor element 201 is subjected to a heat treatment. According to the method mentioned above, it is possible to obtain the gas sensor element 201 in which Rh is existent on a particle surface of the oxide layer 205 and is not existent on a connection portion between particles, as shown in FIG. 11. If the thus obtained gas sensor element 201 is used for an NOx concentration measurement, it is possible to not only to reduce an interference of SOx, HC, CO gases in the case of the NOx concentration measurement but also to eliminate a temperature dependency in the case of the NOx concentration measurement.

As shown in the following experiment, firing the oxide at a temperature higher than 1200° C., controlling a particle size of the oxide layer 205 in a range of larger than 0.2 μm, controlling a porosity of the oxide layer 205 in a range of larger than 20%, and controlling a short diameter (thickness) of the oxide layer 205 in a range of smaller than 3 μm, are preferred to improve further a precision of the NOx concentration measurement, both in the case that a predetermined amount of Ta is added in the oxide layer 205 and in the case that a predetermined amount of Ta is added in the oxide layer 205 and also Rh is supported on a surface of the oxide layer 205.

Hereinafter, an actual experiment in which Ta is added in the oxide layer 205 is shown in the following Experiment 3, and an actual experiment in which Ta is added in the oxide layer 205 and also Rh is supported on a surface of the oxide layer 205 is shown in the following Experiment 4.

Experiment 3

(1) Manufacturing of gas sensor element according to the invention:

At first, according to the following steps (a)–(c), Ta was added in an oxide, and then gas sensor elements 201 according to the present embodiments 21–25 having the construction shown in FIG. 10 were prepared by using the thus obtained Ta added oxide. Moreover, according to the following steps (a)–(d), Ta was added in an oxide, gas sensor elements 201 having the construction shown in FIG. 10 were once prepared by using the thus obtained Ta added oxide, and then gas sensor elements 201 according to the present embodiments 26–31 were prepared by further supporting Rh on the oxide of the thus prepared gas sensor elements.

(a) Synthesizing of $SnO_2$:

500 g of $SnCl_4 \cdot xH_2O$ was dissolved in 2 liters of a distilled water. Then, the distilled water in which $SnCl_4 \cdot xH_2O$ was dissolved was stirred by an agitator, and an ammonia solution (28%) was added therein to a level such that the stirred solution became pH 8. Then, a white sedimentation obtained in this case was filtered by sucking it, and the thus obtained white sedimentation was dried by using a heated air blow at 100–120° C. for 15 hours. Further, the dried sedimentation was subjected to a heat treatment in the atmosphere by using a heating furnace. Then, the white sedimentation after the heat treatment was crushed in an alumina mortar to a level such that the thus crushed powders were passed through a sieve having 100 mesh, so as to synthesize $SnO_2$ powders.

(b) Manufacturing of dispersion solution:

The thus obtained $SnO_2$ powders were measured by 3–5 g, and the thus measured $SnO_2$ powders were put in a polymer pot of 500 ml. Moreover, $Ta_2O_3$ powders were also put in the polymer pot. In this case, $Ta_2O_3$ powders were added in such a manner that Ta atoms were in a range of 1–10 atomic % with respect to Sn atoms in $SnO_2$ powders. Further, 400 g of $ZrO_2$ balls having a diameter of 5 mm and 40 ml of ethanol were added in the polymer pot. Then, the polymer pot was set in the crusher to crush the powders in the polymer pot for 16 Hrs. The thus crushed powders were put out from the polymer pot by using 20–40 ml of ethanol. The thus obtained powders were passed through a sieve having 325 mesh, and then kept in a suitable bottle. After that, 20–40 ml of ethanol was vaporized to obtain 30–40 ml of dispersion solution ($SnO_2 + Ta_2O_3$).

(c) Dipping and Firing:

The thus manufactured dispersion solution in the bottle was mixed by an ultrasonic wave from an ultrasonic generator. After that, a sensor body prepared beforehand was dipped in the dispersion solution and was pulled up at a pulling up rate of about 5 mm/min. In this case, the sensor body had a construction such that two platinum wires each having a diameter of 0.3 mm were wound at both ends of an alumina rod having a diameter of 1.2 mm and a length of 5 mm. The dipping was repeated at several times to obtain an oxide layer having a predetermined thickness on a surface of the alumina rod. After that, the sensor body with the oxide layer was fired by means of an electric furnace, in which the atmosphere was filled, at 1000–1200° C. for 2 hours, as shown in the following Table 4, so as to obtain gas sensor elements according to the invention (present embodiments 21–25) in which Ta was added in the oxide layer. Then, particle size, porosity and thickness were measured with respect to the gas sensor elements according to the present embodiments 21–25 and the gas sensor elements to which Rh was supported at the next step.

(d) Supporting of Rh:

An aqueous solution, in which rhodium nitrate was dissolved in a water in such a manner that Rh volume concentration was 1 ppm-1% as shown in the following Table 4, was prepared. Then, the gas sensor elements each having $SnO_2$-Ta fired body according to the steps (a)–(c) mentioned above were immersed in the thus prepared aqueous solution. After that, the gas sensor elements were pulled up from the aqueous solution. The gas sensor elements were then subjected to a heat treatment by means of an electric furnace, in which the atmosphere was filled, at 800° C. for 2 hours. Then, the gas sensor elements according to the invention (present embodiments 26–31), in which Ta was added in the oxide layer and Rh was supported on the oxide layer, were obtained. (2) Manufacturing of gas sensor element according to the comparative embodiment:

(a) Manufacturing of comparative embodiment including only Ta:

According to the same manufacturing method as that of the present embodiment mentioned above, the gas sensor element according to the comparative embodiment 21 having the oxide layer made of $SnO_2$ powders only, and the gas sensor elements according to the comparative embodiments 22 and 23 in which 0.5 atomic % of Ta and 15 atomic % of Ta were added in $SnO_2$ respectively were manufactured by using $SnO_2$ powders including no Ta as a raw material. Then, as is the same as the present embodiment, particle size, porosity and thickness of the oxide layer were measured with respect to respective gas sensor elements.

(b) Manufacturing of comparative embodiment including Ta and Rh:

In a flask, $SnO_2$ powders were mixed with a rhodium nitrate solution in which Rh concentration was controlled at 10 ppm and a distilled water having a volume ten times larger than that of $SnO_2$ powders. In the flask, an ultrasonic wave was applied to the mixed solution by means of an ultrasonic generator so as to agitate the mixed solution in an uniform state. Then, the flask was set in a rotary evaporator so as to vaporize and dry the mixed solution at 60–70° C. to obtain powders. After that, the dried powders were put in an alumina crucible and were subjected to a heat treatment in an electric furnace, in which the atmosphere was filled, at 60° C. for 1 Hr. The powders after the heat treatment were crushed in an alumina mortar finely so as to obtain $SnO_2$ powders in which Rh was added. After that, the dispersion solution manufacturing (1)-(b) mentioned above and the dipping and firing (1)-(c) mentioned above were performed so as to obtain the gas sensor element according to the comparative embodiment 24. Then, as is the same as the present embodiment, particle size, porosity and thickness of the oxide layer were measured with respect to the thus obtained gas sensor element respectively.

(3) Estimation of present embodiment and comparative embodiment:

With respect to the thus prepared gas sensor elements according to the present embodiment and the comparative embodiment, an interference rate and a temperature dependency were measured. In this case, the interference rate means a rate of interference of CO, $SO_2$ or $CH_4$, when the NOx concentration measurement was performed with respect to an interference gas in which predetermined amounts of CO, $SO_2$ or $CH_4$ were included in a reference gas i.e. a base gas (the atmosphere) including 100 ppb of NO.

The interference rate is calculated from the following formula: interference rate=|R-r|/(R-RO), wherein RO: resistance value measured by the gas sensor elements according to the present embodiment and the comparative embodiment with respect to the base gas, R: resistance value measured by the gas sensor elements according to the present embodiment and the comparative embodiment with respect to the reference gas, and r: resistance value measured by the gas sensor elements according to the present embodiment and the comparative embodiment with respect to the interference gas. Moreover, the temperature dependency was defined as a temperature variation when an NOx concentration varied by ±1%. In this case, the temperature dependency was measured in the case of 0 ppb of NO and 100 ppb of NO. The results were shown in Table 4.

TABLE 4(a)

|  |  | Present embodiment 21 | Present embodiment 22 | Present embodiment 23 | Present embodiment 24 | Present embodiment 25 | Present embodiment 26 | Present embodiment 27 | Present embodiment 28 |
|---|---|---|---|---|---|---|---|---|---|
| Oxide |  | $SnO_2$ | $SnO_2$ | $SnO_2$ | $SnO_2$ | $SnO_2$ | $SnO_2$ | $SnO_2$ | $SnO_2$ |
| Ta addition amount (at %) |  | 1 | 5 | 10 | 1 | 1 | 1 | 1 | 1 |
| Rh solution concentration |  | — | — | — | — | — | 0.5 ppm | 1 ppm | 1% |
| Rh addition method |  | — | — | — | — | — | addition after firing | addition after firing | addition after firing |
| Firing temperature (° C.) |  | 1000 | 1000 | 1000 | 1200 | 1000 | 1000 | 1000 | 1000 |
| Element properties | Average particle size ($\mu$m) | <0.1 | <0.1 | <0.1 | >0.2 | <0.1 | <0.1 | <0.1 | <0.1 |
|  | Porosity (%) | 10 | 10 | 10 | 20 | 10 | 10 | 10 | 10 |
|  | Element (thickness) ($\mu$m) | 10 | 10 | 10 | 10 | 3 | 10 | 10 | 10 |
| Interference rate | Co | 0.7 | 0.6 | 0.5 | 0.4 | 0.3 | 0.6 | 0.6 | 0.6 |
|  | $SO_2$ | 0.4 | 0.4 | 0.3 | 0.2 | 0.3 | 0.4 | 0.4 | 0.4 |
|  | $CH_4$ | 0.3 | 0.2 | 0.2 | 0.2 | 0.2 | 0.4 | 0.4 | 0.4 |
| Temperature dependency | NO   0 ppb | ±2.0 | ±2.1 | ±2.5 | ±2.5 | ±2.4 | ±2.4 | ±2.0 | ±2.5 |
|  | NO   1000 ppb | ±1.0 | ±0.9 | ±0.8 | ±1.2 | ±1.1 | ±1.4 | +1.8 | ±2.2 |

TABLE 4(b)

|  |  | Present embodiment 29 | Present embodiment 30 | Present embodiment 31 | Comparative embodiment 21 | Comparative embodiment 22 | Comparative embodiment 23 | Comparative embodiment 24 |
|---|---|---|---|---|---|---|---|---|
| Oxide |  | $SnO_2$ | $SnO_2$ | $SnO_2$ | $SnO_2$ | $SnO_2$ | $SnO_2$ | $SnO_2$ |
| Ta addition amount (at %) |  | 1 | 1 | 1 | 0 | 0.5 | 15 | 1 |
| Rh solution concentration |  | 2% | 10 ppm | 10 ppm | — | — | — | 10 ppm |
| Rh addition method |  | addition after firing | addition after firing | addition after firing | — | — | — | addition before firing |
| Firing temperature (° C.) |  | 1000 | 1200 | 1000 | 1000 | 1000 | 1000 | 1000 |
| Element properties | Average particle size ($\mu$m) | <0.1 | >0.2 | <0.1 | <0.1 | <0.1 | <0.1 | <0.1 |
|  | Porosity (%) | 10 | 20 | 10 | 20 | 20 | 20 | 20 |
|  | Element (thickness) ($\mu$m) | 10 | 10 | 3 | 10 | 10 | 10 | 10 |
| Interference rate | CO | 0.5 | 0.3 | 0.3 | 3 | 2.5 | 2.5 | 0.7 |
|  | $SO_2$ | 0.4 | 0.3 | 0.2 | 2 | 1.5 | 2 | 0.4 |
|  | $CH_4$ | 0.2 | 0.2 | 0.2 | 1.5 | 1 | 2 | 0.3 |
| Temperature dependency | NO   0 ppb | ±2.5 | ±2.5 | ±2.4 | ±0.4 | ±0.5 | ±0.6 | ±0.5 |
|  | NO   1000 ppb | ±1.5 | ±2.2 | ±2.1 | ±0.1 | ±0.3 | ±0.3 | ±0.3 |

From the results shown in Table 4, it is understood that the present embodiments 21–31 have a smaller interference rate with respect to CO, $SO_2$ or $CH_4$ interference gas and are not affected by these interference gases as compared with the comparative embodiments 21–24. Moreover, if compared the present embodiments 21–31, it is understood that it is possible to further improve a precision of an Nox concentration measurement by controlling a firing temperature of the oxide at higher than 1200° C., by controlling a particle size of the oxide layer at larger than 0.2 $\mu$m, by controlling a porosity of the oxide layer at larger than 20%, or by controlling a thickness of the oxide layer at smaller than 3 $\mu$m.

Moreover, from the results shown in Table 4, if the present embodiments 25–31 are compared with the comparative embodiment 24, it is understood that the present embodiments 25–31, in which 1–10 atomic % of Ta is added and Rh is supported on a surface of the oxide by dipping the sensor body in rhodium nitrate solution having Rh volume concentration of 1 ppm–1%, have a smaller temperature dependency as compared with the comparative embodiments 24 in which Ta is added in an amount outside the above range.

FIG. 12 is a schematic view showing one embodiment of an ammonia removing apparatus according to the invention. In the embodiment shown in FIG. 12, an ammonia removing apparatus 211 comprises a vessel 212 having a cylindrical shape, acid compound powders 213 filled in the vessel 212, a cap 214 having a gas inlet 214a, which is arranged at an upstream position of the vessel 212, and a cap 215 having a gas outlet 215a, which is arranged at a downstream position of the vessel 212. As the acid compound powders 213, it is preferred to use tartaric acid, citric acid, boric acid or molybdic acid. In the ammonia removing apparatus 211 shown in FIG. 12, it is possible to remove an ammonia component in the measurement gas without varying an amount of NO or $NO/NO_2$ ratio in the measurement gas by supplying the measurement gas from the gas inlet 214a into the vessel 212 and by discharging the measurement gas passed through the acid compound powders 213 from the gas outlet 215a.

Figure 13:
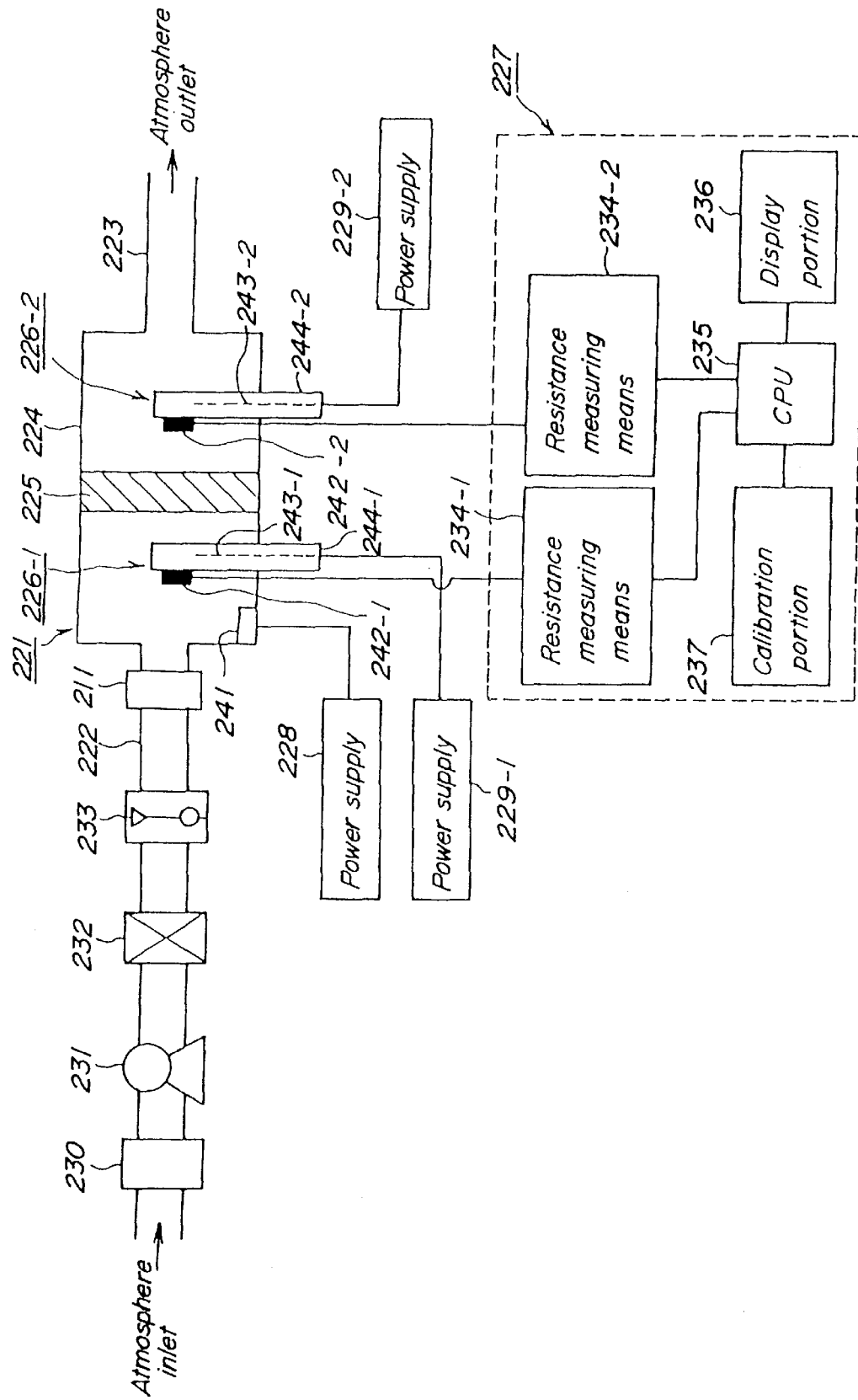
FIG. 13 is a schematic view depicting one embodiment of an NOx sensor having the ammonia removing apparatus shown in FIG. 12 according to the invention.

FIG. 13 is a schematic view showing one embodiment of an apparatus for sensing low concentration NOx in which the ammonia removing apparatus shown in FIG. 12 according to the invention is used. In the embodiment shown in FIG. 13, an apparatus for sensing low concentration NOx 221 is constructed in such a manner that a first sensor element 226-1, a catalyst 225 and a second sensor element 226-2 are arranged in this order from an upstream side in a chamber 224 having an atmosphere inlet pipe 222 and an atmosphere outlet pipe 223, and a measuring portion 227 is arranged outside of the chamber 224. Moreover, a power supply 228 is used for heating the catalyst 225 by means of a heater 241, Power supplies 229-1 and 229-2 are for heating the first and second sensor elements 226-1 and 226-2, respectively by means of heaters 243-1 and 243-2. In the atmosphere inlet pipe 222, there are arranged, from an upstream side of an atmosphere flow, a filter 230 for removing foreign substances, a pump 231, a pressure reducing valve 232 and a flow meter 233, so that a constant atmosphere is always supplied in the chamber 224. Further, the ammonia removing apparatus 211 having the construction shown in FIG. 12 is arranged between the flow meter 233 in the atmosphere inlet pipe 222 and the chamber 224.

The measuring portion 227 comprises resistance measuring means 234-1 and 234-2 arranged corresponding to the first and second sensor elements 226-1 and 226-2, a CPU 235, a display portion 236 and a calibration portion 237. In the measuring portion 227, resistance variations of the first and second sensor elements 226-1 and 226-2 are detected. NO concentration and $NO_2$ concentration in the atmosphere are measured respectively on the basis of the thus detected resistance variations before and after passing the catalyst 225.

The catalyst 225 is used for maintaining partial pressures of NO and $NO_2$ in the atmosphere at an equilibrium state and for removing a combustible gas such as CO from the atmosphere by firing it. As a material of the catalyst 225, it is preferred to use a precious metal or a metal oxide. As a precious metal, it is preferred to use platinum, rhodium or gold. As a metal oxide, it is preferred to use manganese oxide, cobalt oxide or tin oxide. The catalyst 225 is heated by the heater 241 arranged in the chamber 224. Power is supplied to the heater 241 from the power supply 228.

In the first sensor element 226-1 or the second sensor element 226-2, oxide 242-1 or 242-2, whose resistance is varied in response to changes in NOx concentration of the atmosphere if it is contacted with the atmosphere, is arranged on a surface of a ceramic substrate 244-1 or 244-2. In this embodiment, the heater 243-1 or 243-2 is arranged in the ceramic substrate 244-1 or 244-2. As the oxide 242-1 or 242-2, it is preferred to use a metal oxide semiconductor. As the metal oxide semiconductor, it is preferred to use $SnO_2$.

The construction mentioned above is the same as that of the NOx sensor which is disclosed by the applicant in Japanese Patent Application No. 9-80054 except that the ammonia removing apparatus 211 having the construction shown in FIG. 12 in the atmosphere inlet pipe 222, and the functions and effects and a method of sensing an NOx concentration are also same as those of the NOx sensor disclosed in Japanese Patent Application No. 9-80054. In the NOX sensor shown in FIG. 13, in addition to the effects obtained by the NOx sensor disclosed in Japanese Patent Application No. 9-80054, it is possible to further remove an ammonia component in the measurement gas at a position upstream of the catalyst 225 for keeping $NO/NO_2$ ratio at constant without varying an amount of NOx or $NO/NO_2$ ratio in the measurement gas even if the measurement gas includes an ammonia component. Therefore, it is possible to perform a highly precise NOx concentration measurement.

Hereinafter, an actual experiments will be explained.

Experiment 4

Ammonia removing properties of various acid compounds were investigated by using an examination apparatus shown in FIG. 14. The examination apparatus shown in FIG. 14 was constructed in such a manner that a gas mix apparatus 251, the ammonia removing apparatus 211 having the construction shown in FIG. 12, a catalyst 252 made of platinum heated at 800° C., and a chemiluminecent NOx meter 253 were arranged in this order from an upstream position of an examination gas flow. At first, the examination gas having a chemical composition of $NH_3$:0 ppb, $O_2$:20% and $N_2$:remainder was flowed at a flow rate of 1 litter/minute by means of the gas mix apparatus 211 formed by a mass-flow controller. Then, the examination gas in which $NH_3$ concentration was changed to 900 ppb was started to flow, and an ammonia removing time was measured from a start of the examination gas flow. In the ammonia removing apparatus 211, powders 212 of respective acid compounds shown in Table 5 were filled therein by 5 g, and both ends of the gas vessel 212 were sealed by the caps 214 and 215 made of silicone rubber having the gas inlet 214a and the gas outlet 215a. The examination gas passed through the ammonia removing apparatus 211 was further passed through the catalyst 252 so as to oxidize an ammonia component in the gas to NOx. After that, an NOx concentration in the examination gas passed through the catalyst 252 was measured by the chemiluminecent NOx meter 253 as an ammonia component existent in the examination gas.

A relation between the ammonia removing time after $NH_3$ concentration is changed to 900 ppb and the NOx concentration, in the case that use is made of tartaric acid as the acid compound, is shown in FIG. 15. As clearly understood from the graph shown in FIG. 15, no NOx is detected till 25 minutes from a start of the examination with respect to 900 ppb of ammonia. After 25 minutes elapses, NOx is gradually detected. Then, an NOx concentration is almost constant at 850 ppb after about 35 minutes elapses. This shows that an ammonia component is adsorbed and removed by the tartaric acid during first 25 minutes, and thus time duration is defined as the ammonia removing time in this case. Moreover, after the ammonia removing time, an ammonia component which is beyond an ammonia removing capacity if the tartaric acid is oxidized and is detected as NOx.

The ammonia removing times for various acid compounds are summarized in the following Table 5. From the results shown in Table 5, since the ammonia removing times of the acid compounds mentioned here are longer than that of the blank case in which no acid compound is used, it is understood that the acid compounds mentioned here have an ammonia removing property. In this examination, NOx was not detected for 2 minutes in the blank case. However, this does not show the ammonia removing property, and we think that an ammonia component in the examination gas is adsorbed by the pipe.

TABLE 5

| Oxide composition | Removing time (minute) |
| --- | --- |
| Tartaric acid | 25 |
| Citric acid | 11 |
| Boric acid | 5 |
| Molybdic acid | 5 |
| Blank | 2 |

Experiment 5

An adsorption of NOx and a variation of $NO/NO_2$ ratio in the ammonia removing apparatus 211 were investigated by using an examination apparatus having the construction shown in FIG. 16. Respective constructions used in the examination apparatus shown in FIG. 16 and the examination conditions were same as those of the experiment 4. However, the examination gas had a different chemical composition of NO:500 ppb, $NO_2$:500 ppb, $O_2$:20%, $N_2$:remainder. The examination results were shown in the following Table 6. From the results shown in Table 6, it is understood that, even if various acid compounds are used, the same NOx concentration and $NO/NO_2$ ratio as those of the blank case can be obtained. Therefore, it is confirmed that variations of NOx concentration and $NO/NO_2$ ratio do not occur if the ammonia removing apparatus 211 is used.

TABLE 6

| | Tartaric acid | Citric acid | Boric acid | Molybdic acid | Blank |
| --- | --- | --- | --- | --- | --- |
| NOx | 987 | 990 | 985 | 988 | 988 |
| NO | 498 | 502 | 500 | 501 | 497 |
| $NO_2$ | 487 | 488 | 485 | 487 | 491 |
| $NO/NO_2$ | 1.02 | 1.03 | 1.03 | 1.03 | 1.01 |

From the results shown in the experiment 4 and the experiment 5 mentioned above, it is understood that, all the acid components (tartaric acid, citric acid, boric acid, molybdic acid), which are investigated here, can be used as an ammonia removing material. Especially, since tartaric acid has a large ammonia removing capacity, it is preferred to use tartaric acid as the acid compound for removing an ammonia compound.

Experiment 6

An NOx concentration in a synthesized gas as a sample gas having a chemical composition shown in the following Table 7 were measured by using the NOx sensor including the ammonia removing apparatus 211 having the construction shown in FIG. 12 (present embodiment) and by using the NOx sensor including no ammonia removing apparatus 211 (comparative embodiment). The NOx concentration measurement was performed according to the method disclosed in Japanese Patent Application No. 9-80054 is proposed by the applicant. The results were shown in the following Table 7. From the results shown in Table 7, it is understood that the present embodiment having the ammonia removing apparatus 211 can measure an NOx concentration without being interfered by an ammonia component as compared with the comparative embodiment having no ammonia removing apparatus 211.

TABLE 7

| Sample gas components | NO | 100 ppb |
| --- | --- | --- |
| | $NO_2$ | 100 ppb |
| | $NH_3$ | 50 ppb |
| | $O_2$ | 20% |
| | $N_2$ | (remainder) |
| Present embodiment | NO | 100 ppb |
| | $NO_2$ | 100 ppb |
| Comparative embodiment | NO | 120 ppb |
| | $NO_2$ | 130 ppb |

As clearly understood from the above explanations, according to the apparatus for sensing low concentration NOx according to the first aspect of the invention, an NOx concentration is measured under a condition such that a temperature T of the sensor element is maintained in a range of 500° C.$\leq$T$\leq$800° C. In the preferred embodiment, a water control means further controls a water component in the atmosphere at constant, and the thus controlled atmosphere is contacted with the sensor element. Therefore, an NOx component is adsorbed at an equilibrium state with respect to a response portion, ant thus it is possible to measure a low concentration NOx in a highly precise manner. Moreover, in the apparatus for sensing low concentration NOx according to the second aspect of the invention, an NOx concentration is measured under a condition such that a temperature T of the sensor element is maintained in a range of 500° C.$\leq$T$\leq$800° C. by using the atmosphere which is contacted with the catalyst for maintaining partial pressures of NO and $NO_2$ in the atmosphere at an equilibrium state. In the preferred embodiment, a water control means further controls a water component in the atmosphere at constant, and the thus controlled atmosphere is contacted with the sensor element. Therefore, it is possible to measure a low concentration NOx in the atmosphere in a highly precise manner.

As clearly understood from the above explanations, according to the apparatus for sensing low concentration NOx according to the third aspect of the invention, the NOx measurement module has preferably the catalyst for maintaining partial pressures of NO and $NO_2$ in the measurement gas at an equilibrium state, wherein use is made of two sensor elements. One sensor element is contacted with the measurement gas which is not contacted with the catalyst, and the other sensor element is contacted with the measurement gas which is contacted with the catalyst. In addition, the other gas introduction module, humidity control module, and process and control module are controlled most suitably. Therefore, it is possible to measure a low concentration NOx in the atmosphere in a highly precise manner.

As clearly understood from the above explanations, according to the chamber used for the apparatus for sensing low concentration NOx according to the invention, the first sensor element securing portion, the catalyst accommodating portion, and the second sensor element securing portion are arranged in the chamber main body. The first to fourth through holes communicate therebetween to construct integrally the first sensor element, the catalyst, and the second sensor element in the chamber. Therefore, it is possible to achieve a compact chamber construction as compared with the case when the first sensor element, the catalyst, and the second sensor element are arranged in a chamber having a large inner space.

As clearly understood from the above explanations, according to the gas sensor element and the method of manufacturing the same according to the invention, an influence of SOx gas, HC gas or CO gas during an NOx concentration measurement can be reduced by adding 1–10 atomic % of Ta in the oxide preferably made of $SnO_2$. Moreover, in the preferred embodiment, Rh is existent on a particle surface of the oxide and is not existent on a connection portion between particles in addition to an adding of Ta mentioned above. In this case, it is possible to further eliminate a temperature dependency during the NOx concentration measurement. Therefore, in both cases, it is possible to improve the precision of an NOx concentration measurement of the NOx sensor using the gas sensor element according to the invention.

As clearly understood from the above explanations, according to the ammonia removing apparatus and the NOx sensor utilizing this apparatus the solid acid compound preferably made of tartaric acid, citric acid, boric acid or molybdic acid can remove only an ammonia component without varying a total amount of NOx or partially pressurized of NO and $NO_2$. Moreover, in the NOx sensor according to the invention, only an ammonia component can be removed from the measurement gas without varying a total amount of NOx or partial pressures of NO and $NO_2$ at a position upstream of the catalyst in order to maintain partial pressures of NO and $NO_2$ at constant. Therefore, it is possible to measure the NOx concentration in a highly precise manner.

What is claimed is:

1. A chamber used for an apparatus for sensing low concentration NOx in a measurement gas having, a catalyst arranged to maintain partial pressures of NO and $NO_2$ in the measurement gas at an equilibrium state, and first and second sensor elements arranged in a flow path of the measurement gas, the resistance of each of said first and second sensor elements varying in response to changes in NOx concentration of the measurement gas, said first sensor element being contacted with the measurement gas which is not contacted with said catalyst and said second sensor element being contacted with the measurement gas which is contacted with said catalyst, comprising:

a chamber main body having a gas inlet and a gas outlet of the measurement gas;

a first sensor element securing portion for securing said first sensor element, arranged in said chamber main body;

a catalyst accommodating portion for accommodating said catalyst, arranged in said chamber main body;

a second sensor element securing portion for securing said second sensor element, arranged in said chamber main body; and first, second, third and fourth through holes arranged in said chamber main body in such a manner that said first through hole communicates said gas inlet and said first sensor element securing portion, said second through hole communicates said first sensor element securing portion and said catalyst accommodating portion, said third through hole communicates said catalyst accommodating portion and said second sensor element securing portion, and said fourth through hole communicates said second sensor element securing portion and said gas outlet.

2. The chamber according to claim 1, wherein said catalyst has a construction such that one of a precious metal and a metal oxide is supported on a ceramic honeycomb structural body.

3. The chamber according to claim 1, wherein a sectional area of said second through hole is smaller than that of said first sensor element securing portion.

4. The chamber according to claim 1, wherein said catalyst is heated by heating said chamber main body by means of a heater.

5. An $NO_x$ sensor for sensing an $NO_x$ concentration in a measurement gas, comprising:

a first sensor element comprising an oxide semiconductor;

a catalyst arranged upstream of said first sensor element to maintain partial pressures of NO and $NO_2$ in the measurement gas at an equilibrium state;

a second sensor element comprising an oxide semiconductor arranged upstream of said catalyst; and an ammonia removing apparatus comprising a solid acid compound arranged upstream of said second sensor element.

6. The $NO_x$ sensor recited in claim 5, wherein said ammonia removing apparatus is constructed by filling a powder of said solid acid compound in a vessel.

7. The $NO_x$ sensor recited in claim 5, wherein said solid acid compound comprises at least one of tartaric acid, citric acid, boric acid and molybdic acid.

* * * * *